(12) United States Patent
Liang et al.

(10) Patent No.: US 12,195,476 B2
(45) Date of Patent: Jan. 14, 2025

(54) SYNTHESIS METHOD OF FUROIMIDAZOPYRIDINE COMPOUND, CRYSTAL FORM OF FUROIMIDAZOPYRIDINE COMPOUND, AND CRYSTAL FORM OF SALT THEREOF

(71) Applicant: HANGZHOU HIGHLIGHTLL PHARMACEUTICAL CO., LTD, Zhejiang (CN)

(72) Inventors: Congxin Liang, Jupiter, FL (US); Laibao Wang, Shanghai (CN); Haihui Liu, Shanghai (CN)

(73) Assignee: HANGZHOU HIGHLIGHTLL PHARMACEUTICAL CO., LTD., Zhejiang (CN)

( * ) Notice: Subject to any disclaimer, the term of this patent is extended or adjusted under 35 U.S.C. 154(b) by 650 days.

(21) Appl. No.: 17/615,313

(22) PCT Filed: Apr. 30, 2020

(86) PCT No.: PCT/CN2020/088121
§ 371 (c)(1),
(2) Date: Nov. 30, 2021

(87) PCT Pub. No.: WO2020/244348
PCT Pub. Date: Dec. 10, 2020

(65) Prior Publication Data
US 2022/0227777 A1 Jul. 21, 2022

(30) Foreign Application Priority Data

Jun. 6, 2019 (CN) .......................... 201910490418.8

(51) Int. Cl.
C07D 491/147 (2006.01)
(52) U.S. Cl.
CPC ...... *C07D 491/147* (2013.01); *C07B 2200/13* (2013.01)
(58) Field of Classification Search
CPC .................... C07D 491/147; C07B 2200/13
See application file for complete search history.

(56) References Cited

U.S. PATENT DOCUMENTS

2019/0256523 A1\* 8/2019 Liang ................. C07D 491/147

FOREIGN PATENT DOCUMENTS

| CN | 104918945 A | 9/2015 |
| CN | 108366994 A | 8/2018 |
| JP | 2017514832 A | 6/2017 |
| WO | 2018067422 A1 | 4/2018 |
| WO | 2018112379 A1 | 6/2018 |

OTHER PUBLICATIONS

Extended European Search Report for EP Patent Application No. 23182049.9 dated Sep. 8, 2023; 7 pp.
English translation of the International Search Report for International Application No. PCT/CN2020/088121, mailed Aug. 10, 2020, 3 pages.
Patent Examination Report 1 for New Zealand Patent Application No. 782816 dated Feb. 22, 2024; 4 pp.
Examination Report No. 1 for Australian Patent Application 2020289149 dated Oct. 5, 2022; 6 pp.
Office Action for Mexican Patent Application MX/a/2021/014319 received Feb. 16, 2024; 6 pps.
Caira, Mino R., "Crystalline Polymorphism of Organic Compounds"; Topics in Current Chemistry; vol. 198; 1998; 47 pps.
Braga, Dario, et al., "Crystal Polymorphism and Multiple Crystal Forms"; Chapter in Structure and Bonding; Feb. 2009; 28 pps.
Hilfiker, Rolf, et al., "Relevance of Solid-state Properties for Pharmaceutical Products"; Polymorphism: in the Pharmaceutical Industry; 2006; 20 pps.
Notification of Reasons for Refusal for Japanese Patent Application No. JP2021-572485 drafted Jan. 6, 2023; 9 pp.
Office Action for China Patent Application 202080036439.3 dated Feb. 11, 2023; 9 pp.
First Examination Report for Patent Application IN 202147056195 dated Jan. 12, 2022; 5 pp.
European Extended Search Report for Patent Application EP 20818305.3 dated Feb. 10, 2023; 11 pp.
Caira, Mino R., "Crystalline Polymorphism of Organic Compounds," Current Chemistry, vol. 198, 1998; 46 pp.
Zhang, Yaozhong et al., "ATRP of Methyl Acrylate with Metallic Zinc, Magnesium, and Iron as Reducing Agents and Supplemental Activators," Macromolecules 2011, vol. 44, pp. 683-685.
Office Action for Russian Patent Application No. 202391820/28 mailed Jun. 17, 2024; 4 pp.
Canada Office Action for Patent Application CA 3,142,625 dated Dec. 14, 2022; 10 pp.
Russian Office Action for patent application RU 202192873 mailed Dec. 22, 2022; 5 pp.

\* cited by examiner

*Primary Examiner* — Timothy R Rozof
(74) *Attorney, Agent, or Firm* — Armstrong Teasdale LLP

(57) ABSTRACT

Provided is a method for synthesizing a compound 2-[(2R,5S)-5-[2-[(R)-1-hydroxyethyl]furo[3,2-b]imidazo[4,5-d]pyridin-1-yl]tetrahydropyran-2-yl]acetonitrile as a selective JAK1/TYK2 kinase inhibitor. The compound is prepared by nucleophilic substitution, palladium on carbon reduction, and cyclization reaction using 7-chloro-6-nitrofuro[3,2-b]pyridine as a starting material. The synthesis method has mild reaction conditions, high product yield, and high purity, and is suitable for industrial production. Further provided are a crystal form of the compound, crystal forma of its salts, and their preparation methods. The crystal form of the compound and the crystal forms of its salts have good physical and chemical properties and are suitable for drug development.

27 Claims, 11 Drawing Sheets

SYNTHESIS METHOD OF FUROIMIDAZOPYRIDINE COMPOUND, CRYSTAL FORM OF FUROIMIDAZOPYRIDINE COMPOUND, AND CRYSTAL FORM OF SALT THEREOF

CROSS-REFERENCE TO RELATED APPLICATIONS

This application is a U.S. National Phase Application of PCT/CN2020/088121, filed Apr. 30, 2020, which claims the benefit of priority to CN Application No. 201910490418.8, filed Jun. 6, 2019, the contents of which are hereby expressly incorporated by reference in their entirety.

TECHNICAL FIELD

The present invention relates to the field of drug synthesis, specifically to the synthesis method of the compound 2-[(2R,5S)-5-[2-[(R)-1-hydroxyethyl]furo[3,2-b]imidazo[4,5-d]pyridin-1-yl]tetrahydropyran-2-yl]acetonitrile (hereinafter referred to as compound I) as a selective JAK1/TYK2 kinase inhibitor. The present invention also relates to the crystal form of compound I and its salts and their preparation methods. In addition, the present invention also relates to pharmaceutical compositions and pharmaceutical formulations comprising the crystal form of compound I and/or the crystal form of its salts as well as use of the crystal form of compound I and its salts in treating JAK1/TYK2-related diseases and conditions.

BACKGROUND

Protein kinases represent a family of proteins that play an important role in modulating multiple cell processes and maintaining cell functions. These kinases comprise at least: non-receptor tyrosine kinase, such as Janus kinase family (JAK1, JAK2, JAK3 and TYK2); receptor tyrosine kinase, such as platelet-derived growth factor receptors (PDGFR); and serine/threonine kinase, such as b-RAF.

Janus kinase family includes 4 known family members: JAK1, JAK2, JAK3 and tyrosine kinase 2 (TYK2). These cytoplasmic tyrosine kinases are related to membrane cytokine receptor (such as common γ-chain receptor and glycoprotein 130 (gp130) transmembrane protein) (Murray, *J Immunol.* 178 (5): 2623-2629, 2007). Almost 40 cytokine receptors transmit signals by the combination of these four JAK family members and their 7 downstream substrates: the signal transduction activator of transcription (STAT) family members (Ghoreschi et al., *Immunol Rev.* 228 (1): 273-287, 2009). Cytokine that binds to its receptor activates JAK by trans and/or autophosphorylation. Activated JAK family kinase phosphorylates cytokine receptor residues, generates binding sites for proteins (such as STAT factor and other regulators) containing Src homology 2 (SH2), and activates them. Activated STAT enters the cell nucleus, starts to promote the expression of survival factors, cytokines, chemokines and molecules of white blood cell transport (Schindler et al., *J Biol. Chem.* 282(28):20059-20063, 2007). JAK activation also causes cell proliferation by pathways mediated by phosphoinositide-3-kinase (PI3K) and protein kinase B.

JAK3 and JAK1 are components of common γ-chain cytokine receptor compound, and blocking any one of the two can inhibit signal transduction of inflammatory cytokines (interleukin (IL)-2, 4, 7, 9, 15 and 21) (Ghoreschi et al., *Immunol. Rev.* 228(1):273-287, 2009). In contrast, other pathologically relevant cytokines (such as IL-6) only depend on JAK1. Therefore, JAK1 blocking inhibits signal transduction of many proinflammatory cytokines (Guschin et al, *EMBO J.* 14 (7): 1421-1429, 1995). Clinical efficacy of IL-6 receptor neutralizing antibody—tocilizumab in rheumatoid arthritis (RA) has been reported (Maini et al, *Arthritis Rheum.* 54(9):2817-2829, 2006).

International patent application WO2018067422A1 discloses 1H-furo[3,2-b]imidazo[4,5-d]pyridine derivatives as selective JAK1 kinase inhibitors and preparation methods thereof, wherein compound I and its preparation method is disclosed. The synthesis route is as follows:

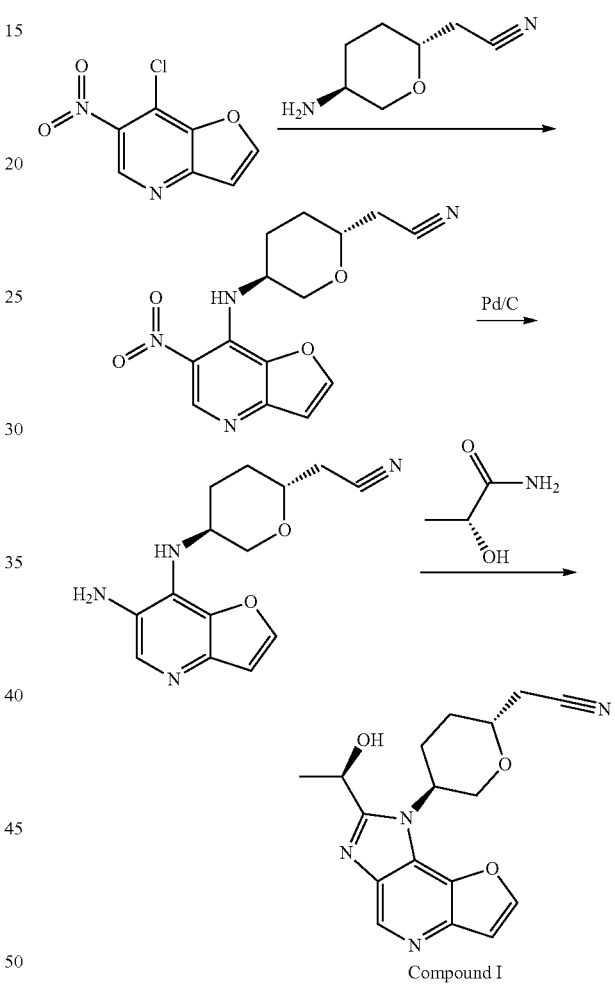

Compound I

Biological tests indicate that compound I is a potent and selective JAK1 inhibitor, demonstrated selective inhibition of IL-6-induced STAT3 phosphorylation and did not show selective inhibition of thrombopoietin-induced STAT3 phosphorylation. However, international patent application WO2018067422A1 does not show the biological activities of TYK2. In addition, the disclosed preparation method of compound I involves high temperature, produces too many impurities, and has low yield, thus is not suitable for large scale production. Therefore, it is necessary to develop a preparation method of compound I with milder reaction conditions, higher yield, higher purity and is suitable for large scale/industrial production.

Currently, there is no report of the crystal form of compound I and its salt in the prior art. Comprehensive and systematic polymorphism screening and a selection of a crystal form that is most suitable for development are indispensable in drug research and development. Accordingly, it is necessary to further screen the crystal forms of compound I and its salts, identify crystal forms with good stabilities, and low hygroscopicities and are suitable for large scale production, providing more and better choices for the subsequent development of the drug.

SUMMARY

The objective of the present invention is to provide a method for preparing a compound of formula I (i.e., compound I) with mild reaction conditions, high product yield and purity and is suitable for industrial production. The synthesis route of the method is as follows:

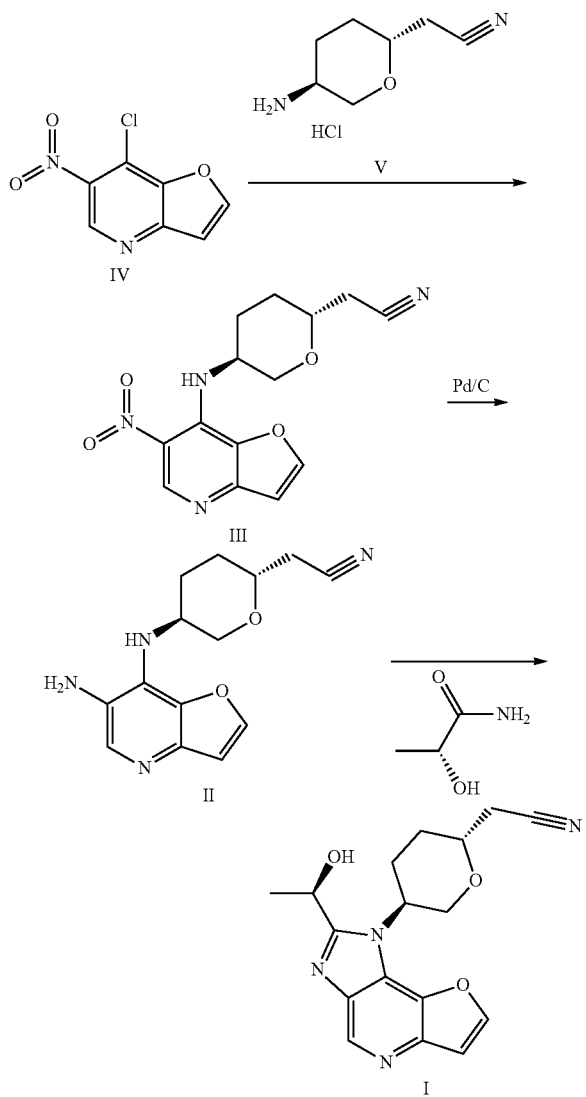

the method comprises the following steps:
step 1:
adding ethanol, a compound of formula IV, a compound of formula V and DIPEA to a reaction container, starting stirring;
heating to raise the temperature to 65-90° C., maintaining the temperature and stirring overnight;

terminating the reaction and lowering the temperature of the system to 15-30° C.; adding water to the system dropwise and then stirring;
filtering and washing the filter cake;
drying the filter cake to obtain a compound of formula III;
step 2:
adding tetrahydrofuran (THF), the compound of formula III obtained in step 1 and palladium on carbon to a reaction container;
purging the system with nitrogen and then hydrogen;
maintaining the temperature between 20-35° C. and stirring for 16-120 hours under 0.1-1.0 MPa hydrogen pressure;
after the reaction is completed, filtering the reaction liquid and washing the filter cake; combining the filtrate and concentrating to obtain a compound of formula II concentrate; step 3:
adding THF, (R)-lactamide and $Et_3O$—$BF_4$ to a first reaction container, starting to stir and dissolving for later use;
adding the above compound of formula II concentrate and ethanol to a second reaction container, and heating the materials of the second container to 40-85° C.;
adding materials in the first reaction container to the second reaction container dropwise, after the addition is completed, maintaining the temperature between 40-85° C. and reacting the mixed materials in the second reaction container for 0.5-6 hours;
after the reaction is completed, adjusting the pH value of the system to 1-3, extracting with an organic solvent or organic solvents, discarding the organic phase, adjusting the pH of the aqueous phase to 9-10 with inorganic alkali aqueous solution, filtering, drying the filter cake to obtain a compound of formula I.

In a preferred embodiment, in the above step 1:
the volume mass ratio (mL/g) of ethanol to the compound of formula IV is between 5:1 and 20:1, preferably 10:1;
the molar ratio of the compound of formula IV, the compound of formula V and DIPEA is 1:1-1.1:2-3, preferably 1:1.01:2.2;
after starting stirring, under nitrogen protection, heating to raise the temperature to 65-90° C., preferably 70-90° C., more preferably 70-80° C., maintaining the temperature and stirring for 5-16 hours, preferably 10-16 hours;
after terminating the reaction, lowering the temperature of the system to 15-25° C. the volume mass ratio (mL/g) of water added to the system to the compound of formula IV is between 10:1 and 20:1, preferably 15:1;
after adding water to the system, stirring for 2-6 hours, preferably 4 hours, at a temperature between 0-30° C., preferably 5-15° C., more preferably 5-10° C.;
the filter cake is washed with ethanol solution, the volume ratio (mL/mL) of ethanol to water in the ethanol solution is between 1:1 and 1:2, preferably 1:1.5-1:2;
the volume mass ratio (mL/g) of the ethanol solution to the compound of formula IV is between 2:1 and 10:1, preferably 2:1-5:1, more preferably 2:1-3:1;
the filter cake is dried under vacuum or dried with an air blower at a temperature between 45-55° C., preferably 50° C.

In a preferred embodiment, in the above step 2:
the volume mass ratio (mL/g) of THF to the compound of formula III is between 10:1 and 70:1, preferably 20:1-70:1;
the palladium on carbon is 5% Pd/C, 50% wet palladium on carbon, the mass ratio (g/g) of the palladium on carbon to the compound of formula III is between 0.15:1 and 0.16:1, preferably 0.15:1;

maintaining the temperature at 25-35° C. and stirring for 24-96 hours under 0.5-1.0 MPa hydrogen pressure;

the filter cake is washed with THF, the compound of formula II concentrate obtained by combining the filtrate and concentrating is the compound of formula II in THF, the volume mass ratio (mL/g) of THF for washing to the compound of formula II is between 2:1 and 4:1, preferably 2:1-3:1 (the mass of the compound of formula II calculated according to 100% yield in step 2); preferably, exchanging the compound of formula II in THF with ethanol to obtain the compound of formula II in ethanol, wherein the volume mass ratio (mL/g) of ethanol to the compound of formula II is between 2:1 and 5:1, preferably 2:1-4:1, more preferably 2:1-3:1 (the mass of the compound of formula II calculated according to 100% yield in step 2).

In a preferred embodiment, in the above step 3:

the volume mass ratio (mL/g) of THF to the compound of formula II concentrate is between 6:1 and 12:1;

the molar ratio of the compound of formula II concentrate, (R)-lactamide and $Et_3O$—$BF_4$ is 1:4-5:4-5;

the volume mass ratio (mL/g) of ethanol to the compound of formula II concentrate is between 10:1 and 16:1, preferably 14:1;

after adding the compound of formula II concentrate and ethanol to the second reaction container, under nitrogen protection, heating the materials in the second reaction container to 40-85° C., preferably 45-70° C., more preferably 45-50° C.;

maintaining the temperature at 45-70° C., preferably 45-50° C., and reacting the mixed materials in the second reaction container for 2-5 hours, preferably 3 hours;

after the reaction is completed, adjusting the pH of the system to 1-3 with hydrochloric acid, the hydrochloric acid is 1M HCl or 12M HCl, preferably 12M HCl; the inorganic alkali aqueous solution is saturated sodium carbonate solution or saturated potassium carbonate solution, preferably saturated potassium carbonate solution;

after the reaction is completed, the organic solvent used for the extraction is dichloromethane or ethyl acetate;

the filter cake is dried under vacuum or dried with an air blower at a temperature between 50-55° C.

In a preferred embodiment, the compound of formula I obtained in the above step 3 is separated and purified by column chromatography, wherein a mixed solution of ethyl acetate and ethanol is used as an eluent ($V_{EA}:V_{EtOH}$=100:1-30:1, mL/mL).

Another objective of the present invention is to provide a crystal form of a compound of formula I, which is called crystal form 1 of a compound of formula I hereinafter.

Crystal form 1 of a compound of formula I of the present invention has an X-ray powder diffraction pattern showing characteristic peaks at 2theta angles of 8.5°±0.2°, 14.8°±0.2° and 16.10°±0.2°.

In a preferred embodiment, the X-ray powder diffraction pattern of crystal form 1 of a compound of formula I shows characteristic peaks at 2theta angles of 8.5°±0.2°, 14.8°±0.2°, 16.1°±0.2°, 17.1°±0.2°, 18.8°±0.2° and 19.6°±0.2°.

In a further preferred embodiment, the X-ray powder diffraction pattern of crystal form 1 of a compound of formula I shows characteristic peaks at 2theta angles of 8.5°±0.2°, 14.8°±0.2°, 16.1°±0.2°, 17.1°±0.2°, 18.8°±0.2°, 19.6°±0.2°, 23.8°±0.2°, 25.3°±0.2° and 26.1°±0.2°.

Non-restrictively, the X-ray powder diffraction data of crystal form 1 of a compound of formula I are shown in Table 1.

TABLE 1

| Diffraction angle 2θ | d value | Relative intensity % (Calculated according to peak height) |
|---|---|---|
| 8.5 | 10.3378 | 100 |
| 14.8 | 5.9874 | 15.7 |
| 16.1 | 5.5068 | 16.1 |
| 17.1 | 5.1787 | 11.5 |
| 18.8 | 4.7149 | 17.9 |
| 19.6 | 4.5237 | 26.1 |
| 23.8 | 3.7351 | 19.3 |
| 25.3 | 3.519 | 24.1 |
| 26.1 | 3.4072 | 16.1 |

Non-restrictively, the X-ray powder diffraction (XRPD) pattern of crystal form 1 of a compound of formula I of the invention is shown in FIG. 1.

Non-restrictively, the differential scanning calorimetry (DSC) thermogram of crystal form 1 of a compound of formula I of the invention is shown in FIG. 2A. The DSC thermogram shows that the initial melting point of crystal form 1 of a compound of formula I of the invention is 160.76° C. and a wide endothermic peak at 91.85° C. is a dehydrated solvent peak. Non-restrictively, thermogravimetric analysis (TGA) thermogram of crystal form 1 of a compound of formula I of the invention is shown in FIG. 3. The TGA thermogram shows that there is a 5.353% weight loss step of crystal form 1 of a compound of formula I of the invention from 25° C. to 133° C., corresponding to a weight percentage of loss of one water molecule.

Non-restrictively, the dynamic vapor sorption (DVS) isotherm plot of crystal form 1 of a compound of formula I of the invention is shown in FIG. 4. The DVS isotherm plot shows a 5.2% weight gain of crystal form 1 of the compound of formula I of the invention by moisture absorption from 0% RH-95% RH, indicating that the sample is hygroscopic, but water cannot be completely removed during desorption (2% remaining).

The present invention provides a method for preparing crystal form I of a compound of formula I, specifically, the method is described as follows:

method 1:

dissolving a compound of formula I in a solvent, stirring at room temperature, adding water to the above solution of the compound of formula I, stirring, filtering, and drying to obtain crystal form 1 of the compound of formula I.

In a preferred embodiment, the solvent is selected from the group consisting of acetone, methanol, water and any combinations thereof, the solvent is preferably acetone, or a mixed solvent of methanol and water, or a mixed solvent of acetone and water, wherein the volume ratio (mL/mL) of methanol to water in the mixed solvent of methanol and water is 30:1-1:1, preferably 9:1; the volume ratio (mL/mL) of acetone to water in the mixed solvent of acetone and water is 6:1-1:1, preferably 4:1.

In a preferred embodiment, the volume mass ratio (mL/g) of the solvent to the compound of formula I is 20:1-45:1; and the volume mass ratio (mL/g) of water added to the solution of the compound of formula I to the compound of formula I is 20:1-90:1.

In a preferred embodiment, the compound of formula I is dissolved in the solvent at 50-60° C.

In a preferred embodiment, after dissolving the compound of formula I in the solvent, stirring at room temperature for 0.5-24 hours;

In a preferred embodiment, after adding water to the solution of the compound of formula I, stirring at room temperature for 0.5-24 hours, then cooling to 5-15° C. and stirring for 1-4 hours.

Method 2:
  adding a solvent to a compound of formula I, obtaining suspension of the compound of formula I by ultrasonication, protecting the above suspension from light, stirring, centrifuging, collecting the solid to obtain crystal form 1 of the compound of formula I.

In a preferred embodiment, the solvent is selected from the group consisting of THF, methyl tertiary-butyl ether, water, acetone, isopropanol, dichloromethane, ethanol and any combinations thereof.

In a preferred embodiment, the suspension of the compound of formula I is stirred at room temperature or at 45-55° C., preferably 50° C.

In a preferred embodiment, the suspension of the compound of formula I is protected from light and stirred for 6-10 days.

Method 3:
  adding solvent to a compound of formula I, stirring at 50-60° C. to dissolve and obtaining solution of the compound of formula I, filtering the above solution when the solution is still hot, then cooling and crystallizing the filtrate between −20-10° C., centrifuging, then collecting the solid to obtain crystal form 1 of the compound of formula I.

In a preferred embodiment, the solvent is selected from the group consisting of acetone, THF, dichloromethane and any combinations thereof.

In a preferred embodiment, after filtering the solution of the compound of formula I when the solution is still hot, cooling the solution to room temperature at 6° C./h slowly, then cooling and crystallizing between −20-10° C., preferably 2-8° C.

Method 4:
  adding a first solvent to a compound of formula I, obtaining supersaturated solution of the compound of formula I by ultrasonication, filtering, adding a second solvent to the filtrate and stirring, centrifuging, then collecting the solid to obtain crystal form 1 of the compound of formula I.

In a preferred embodiment, the first solvent is selected from the group consisting of methanol, ethanol, THF, acetone, isopropanol and any combinations thereof, the second solvent is selected from the group consisting of water, methyl tertiary-butyl ether, dichloromethane and any combinations thereof;

In a preferred embodiment, the volume ratio (mL/mL) of the first solvent to the second solvent is 1:5-1:20, preferably 1:10.

Another objective of the present invention is to provide crystal forms of a compound of formula I, specifically, a crystal form of a hydrochloride, a crystal form of a sulfate, a crystal form of a hydrobromide, a crystal form of a phosphate of a compound of formula I, which are named as crystal form A of a hydrochloride, crystal form B of a sulfate, crystal form C of a hydrobromide, crystal form D of a phosphate of a compound of formula I hereinafter.

Crystal form A of a hydrochloride of a compound of formula I of the present invention has an X-ray powder diffraction pattern showing characteristic peaks at 2theta angles of 6.4°±0.2°, 12.8°±0.2°, 14.2°±0.2° and 19.0°±0.2°.

In a preferred embodiment, the X-ray powder diffraction pattern of crystal form A of a hydrochloride of a compound of formula I of the present invention shows characteristic peaks at 2theta angles of 6.4°±0.2°, 8.5°±0.2°, 11.6°±0.2°, 12.8°±0.2°, 14.2°±0.2°, 17.1°±0.2° and 19.0°±0.2°.

In a further preferred embodiment, the X-ray powder diffraction pattern of crystal form A of a hydrochloride of a compound of formula I shows characteristic peaks at 2theta angles of 6.4°±0.2°, 8.5°±0.2°, 11.6°±0.2°, 12.8°±0.2°, 14.2°±0.2°, 17.1°±0.2°, 19.0°±0.2°, 19.7°±0.2°, 21.3°±0.2° and 24.5°±0.2°.

Non-restrictively, the X-ray powder diffraction data of crystal form A of a hydrochloride of a compound of formula I of the present invention are shown in Table 2.

TABLE 2

| Diffraction angle 2θ | d value | Relative intensity % (Calculated according to peak height) |
|---|---|---|
| 6.4 | 13.8 | 100 |
| 8.5 | 10.3 | 10.8 |
| 11.6 | 7.6 | 9 |
| 12.8 | 6.9 | 64.9 |
| 14.2 | 6.2 | 19.7 |
| 17.1 | 5.2 | 10.6 |
| 19.0 | 4.7 | 40.3 |
| 19.7 | 4.5 | 10.5 |
| 21.3 | 4.2 | 9.4 |
| 24.5 | 3.6 | 40.4 |

Non-restrictively, the XRPD pattern of crystal form A of a hydrochloride of a compound of formula I of the present invention are shown in FIG. 5.

Non-restrictively, DSC thermogram of crystal form A of a hydrochloride of a compound of formula I of the present invention are shown in FIG. 6.

The present invention provides a method for preparing crystal form A of a hydrochloride of a compound of formula I, specifically the method is described as follows:
  dissolving a compound of formula I in a solvent to obtain solution of the compound of formula I, adding hydrochloric acid in ethanol to the above solution of the compound of formula I under stirring, stirring, then centrifuging, collecting the solid and drying to obtain crystal form A of a hydrochloride of a compound of formula I.

In a preferred embodiment, the compound of formula I is dissolved in a solvent under ultrasonication and heating.

In a preferred embodiment, the solvent is selected from the group consisting of ethanol, acetone, acetonitrile, isopropanol and any combinations thereof.

In a preferred embodiment, the concentration of the hydrochloric acid in ethanol is 30-60 mg/mL, preferably 50 mg/mL.

In a preferred embodiment, after adding the hydrochloric acid in ethanol, stirring at room temperature for 4-24 hours.

Crystal form B of a sulfate of a compound of formula I has an X-ray powder diffraction pattern showing characteristic peaks at 2theta angles of 12.2°±0.2°, 17.1°±0.2°, 18.4°±0.2° and 20.10°±0.2°.

In a preferred embodiment, the X-ray powder diffraction pattern of crystal form B of a sulfate of a compound of formula I shows characteristic peaks at 2theta angles of 12.2°±0.2°, 17.1°±0.2°, 18.4°±0.2°, 19.6°±0.2°, 20.10°±0.2°, 20.6°±0.2° and 22.10°±0.2°.

In a preferred embodiment, the X-ray powder diffraction pattern of crystal form B of a sulfate of a compound of formula I shows characteristic peaks at 2theta angles of 12.2°±0.2°, 17.1°±0.2°, 18.4°±0.2°, 19.6°±0.2°, 20.1°±0.2°, 20.6°±0.2°, 22.1°±0.2°, 23.5°±0.2°, 26.8°±0.2° and 29.3°±0.2°.

Non-restrictively, the X-ray powder diffraction data of crystal form B of a sulfate of a compound of formula I of the present invention are shown in Table 3.

TABLE 3

| Diffraction angle 2θ | d value | Relative intensity % (Calculated according to peak height) |
|---|---|---|
| 12.2 | 7.3 | 42.1 |
| 17.1 | 5.2 | 42.0 |
| 18.4 | 4.8 | 100 |
| 19.6 | 4.5 | 10.6 |
| 20.1 | 4.4 | 75.3 |
| 20.6 | 4.3 | 34.1 |
| 22.1 | 4.0 | 48.5 |
| 23.5 | 3.8 | 37.9 |
| 26.8 | 3.3 | 23.7 |
| 29.3 | 3.0 | 19.1 |

Non-restrictively, the XRPD pattern of crystal form B of a sulfate of a compound of formula I of the present invention are shown in FIG. 7.

Non-restrictively, the DSC thermogram of crystal form B of a sulfate of a compound of formula I of the present invention are shown in FIG. 8.

Non-restrictively, the TGA thermogram of crystal form B of a sulfate of a compound of formula I of the present invention are shown in FIG. 9.

Non-restrictively, the DVS isotherm plot of crystal form B of a sulfate of a compound of formula I of the present invention are shown in FIG. 10.

The present invention provides a method for preparing crystal form B of a sulfate of a compound of formula I, specifically, the method is described as follows:

dissolving a compound of formula I in a solvent to obtain solution of the compound of formula I, adding sulfuric acid in ethanol to the above solution of the compound of formula I under stirring, stirring, then centrifuging, collecting the solid and drying to obtain crystal form B of a sulfate of a compound of formula I.

In a preferred embodiment, the compound of formula I is dissolved in a solvent under ultrasonication and heating;

In a preferred embodiment, the solvent is selected from the group consisting of ethanol, acetone, acetonitrile, isopropanol and any combinations thereof.

In a preferred embodiment, the concentration of the sulfuric acid in ethanol is 30-60 mg/mL, preferably 50 mg/mL.

In a preferred embodiment, after adding the sulfuric acid in ethanol, stirring at room temperature for 4-24 hours.

Crystal form C of a hydrobromide of a compound of formula I of the present invention has an X-ray powder diffraction pattern showing characteristic peaks at 2theta angles of 6.3°±0.2°, 12.6°±0.2° and 18.9°±0.2°.

In a preferred embodiment, the X-ray powder diffraction pattern of crystal form C of a hydrobromide of a compound of formula I shows characteristic peaks at 2theta angles of 6.3°±0.2°, 8.5°±0.2°, 12.6°±0.2°, 18.9°±0.2°, 21.3°±0.2°, 24.4°±0.2° and 25.2°±0.2°.

Non-restrictively, the X-ray powder diffraction data of crystal form C of a hydrobromide of a compound of formula I of the present invention are shown in Table 4.

TABLE 4

| Diffraction angle 2θ | d value | Relative intensity % (Calculated according to peak height) |
|---|---|---|
| 6.3 | 14.1 | 100 |
| 8.5 | 10.3 | 7.9 |
| 12.6 | 7.0 | 11.4 |
| 18.9 | 4.7 | 29.5 |
| 21.3 | 4.2 | 10.0 |
| 24.4 | 3.6 | 23.8 |
| 25.2 | 3.5 | 5.9 |

Non-restrictively, the XRPD pattern of crystal form C of a hydrobromide of a compound of formula I of the present invention are shown in FIG. 11.

Non-restrictively, the DSC thermogram of crystal form C of a hydrobromide of a compound of formula I of the present invention are shown in FIG. 12.

The present invention provides a method for preparing crystal form C of a hydrobromide of a compound of formula I, specifically, the method is described as follows:

dissolving a compound of formula I in a solvent to obtain solution of the compound of formula I, adding hydrobromic acid in ethanol to the above solution of the compound of formula I under stirring, stirring, then centrifuging, collecting the solid and drying to obtain crystal form C of a hydrobromide of a compound of formula I.

In a preferred embodiment, the compound of formula I is dissolved in a solvent under ultrasonication and heating.

In a preferred embodiment, the solvent is selected from the group consisting of ethanol, acetone, acetonitrile, isopropanol and any combinations thereof.

In a preferred embodiment, the concentration of the hydrobromic acid in ethanol is 30-60 mg/mL, preferably 50 mg/mL.

In a preferred embodiment, after adding the hydrobromic acid in ethanol, stirring at room temperature for 4-24 hours.

Crystal form D of a phosphate of a compound of formula I has an X-ray powder diffraction pattern showing characteristic peaks at 2theta angles of 6.1°±0.2°, 10.9°±0.2° and 12.2°±0.2°.

In a preferred embodiment, the X-ray powder diffraction pattern of crystal form D of a phosphate of a compound of formula I shows characteristic peaks at 2theta angles of 6.1°±0.2°, 10.90±0.2°, 11.70±0.2° and 12.20±0.2°.

Non-restrictively, the X-ray powder diffraction data of crystal form D of a phosphate of a compound of formula I of the present invention are shown in Table 5.

TABLE 5

| Diffraction angle 2θ | d value | Relative intensity % (Calculated according to peak height) |
|---|---|---|
| 6.1 | 14.5 | 100 |
| 10.9 | 8.1 | 19.5 |
| 11.7 | 7.5 | 8.9 |
| 12.2 | 7.3 | 11.8 |

Non-restrictively, the XRPD pattern of crystal form D of a phosphate of a compound of formula I of the present invention are shown in FIG. 13.

Non-restrictively, the DSC thermogram of crystal form D of a phosphate of a compound of formula I of the present invention are shown in FIG. 14.

Non-restrictively, the TGA thermogram of crystal form D of a phosphate of a compound of formula I of the present invention are shown in FIG. 15.

Non-restrictively, the DVS isotherm plot of crystal form D of a phosphate of a compound of formula I of the present invention are shown in FIG. 16.

The present invention provides a method for preparing crystal form D of a phosphate of a compound of formula I, specifically, the method is described as follows:

dissolving a compound of formula I in a first solvent to obtain solution of the compound of formula I, adding phosphoric acid in ethanol to the above solution of the compound of formula I under stirring, stirring, then centrifuging, collecting the solid, adding a second solvent to the collected solid, stirring, then centrifuging, collecting the solid and drying to obtain crystal form D of a phosphate of a compound of formula I.

In a preferred embodiment, the compound of formula I is dissolved in the first solvent under ultrasonication and heating.

In a preferred embodiment, the first solvent is selected from the group consisting of ethanol, acetone, acetonitrile, isopropanol and any combinations thereof; the second solvent is a mixed solvent of acetone and water, wherein the volume ratio (mL/mL) of acetone to water is 7:1-9:1.

In a preferred embodiment, the concentration of the phosphoric acid in ethanol is 30-60 mg/mL, preferably 50 mg/mL.

In a preferred embodiment, after adding the phosphoric acid in ethanol, stirring at room temperature for 4-24 hours; after adding the second solvent, stirring overnight at room temperature.

The present invention also provides a pharmaceutical composition comprising crystal form 1 of a compound of formula I, crystal form A of a hydrochloride of a compound of formula I, crystal form B of a sulfate of a compound of formula I, crystal form C of a hydrobromide of a compound of formula I and/or crystal form D of a phosphate of a compound of formula I, as well as a pharmaceutical formulation comprising crystal form 1 of a compound of formula I, crystal form A of a hydrochloride of a compound of formula I, crystal form B of a sulfate of a compound of formula I, crystal form C of a hydrobromide of a compound of formula I and/or crystal form D of a phosphate of a compound of formula I.

The present invention also provides use of crystal form 1 of a compound of formula I, crystal form A of a hydrochloride of a compound of formula I, crystal form B of a sulfate of a compound of formula I, crystal form C of a hydrobromide of a compound of formula I and/or crystal form D of a phosphate of a compound of formula I in preparing medicaments for treating JAK1/TYK2-related diseases or conditions, wherein the diseases or conditions are autoimmune diseases or disorders, such as rheumatoid arthritis or inflammatory diseases or disorders, and cancers or tumor proliferative diseases or disorders.

EMBODIMENTS

Figure 1:
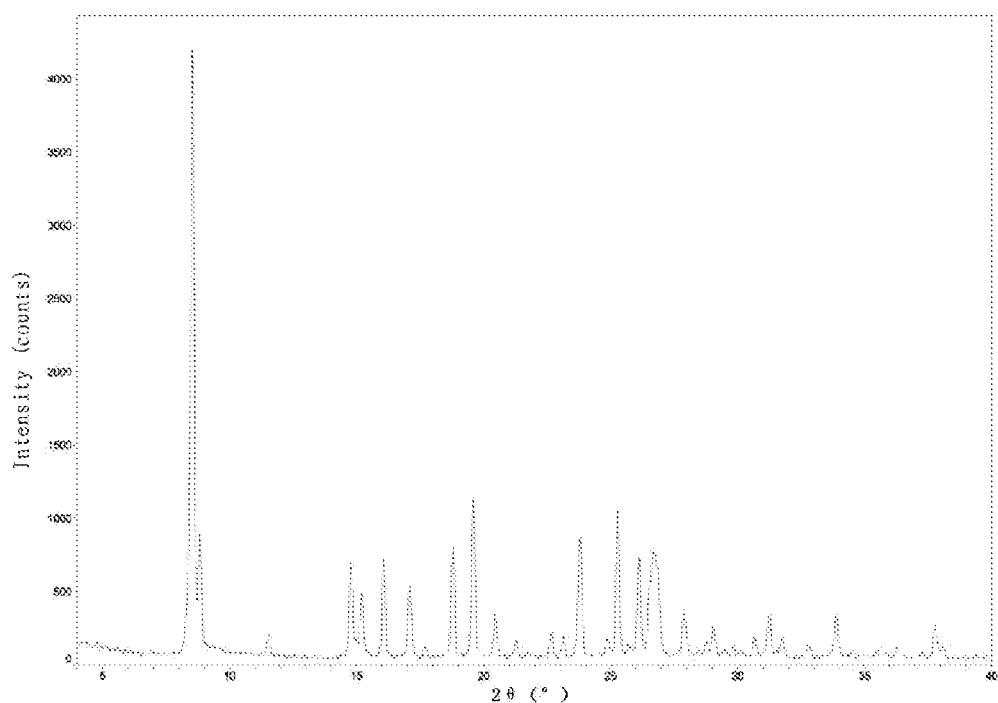
FIG. 1 is the XRPD pattern of crystal form 1 of a compound of formula I of the present invention.

The following examples further explain the invention, however, the examples don't constitute a restriction or limitation to the scope of the invention.

Information and using conditions of the instruments used in the invention are as follows

| No. | Instrument | Model | Manufacturer | Test procedure |
|---|---|---|---|---|
| 1 | High performance liquid | Agilent 1200, DAD | Agilent | Instrument: Agilent 1200 DAD HPLC System or Similar configuration |

-continued

| No. | Instrument | Model | Manufacturer | Test procedure |
|---|---|---|---|---|
| | chromatograph (UPLC) | | | Column: Waters XBridge Shield RP18 4.6 × 150 mm, 3.5 μm Mobile phase: A: 0.05% phosphoric acid aqueous solution; B: Acetonitrile |
| 2 | LC-MS | Agilent 1200 | Agilent | Instrument: Agilent 1200 HPLC/6100 SQ System Column: Agilent XDB-C18, 4.6 mm × 50 mm, 1.8 μm Mobile phase: A: 0.05% TFA in water; B: 0.05% TFA in acetonitrile |
| 3 | ¹HNMR | AVANCEIII400 MHz | BRUKER | Instrument: BRUKER AVANCE III 400 MHz Ultrashield-Plus Digital NMR Spectroscopy Experiment: N PROTON 1H experiment (default parameters) |
| 4 | X-ray powder diffractometer (XRPD) | D8 Advance | BRUKER | Light source is CuK. X-ray intensity is 40 KV/40 mA. Scanning mode is Theta-theta. Scanning angle range is 4-40°. Step length is 0.05°. Scanning speed is 0.5 seconds/step. |
| 5 | Differential scanning calorimeter (DSC) | Q1000 | TA | Weighing 2-4 mg of sample, transferring to an unsealed aluminum pan, the equilibrium of the sample is reached in nitrogen flow (50 mL/min) at 25° C., raising the temperature from 25° C. to 300° C. at 10° C./min. |
| 6 | Thermogravimetric analyzer (TGA) | Q500 | TA | Weighing 10-20 mg of sample, transferring to a platinum sample plate, raising the temperature from 25° C. to 300° C. at 10° C./min in sample nitrogen flow (60 mL/min) and balance nitrogen flow (40 mL/min). |
| 7 | Dynamic vapor sorption analyzer (DVS) | Advantage 1 | Surface Measurement System | Weighing about 10 mg of sample, setting the temperature at 25° C., drying for 60 minutes at a humidity of 0% RH. and determining the moisture absorption characteristics of samples when the humidity changes from 0% RH to 95% RH, and dehumidification characteristics of samples when the humidity changes from 95% RH to 0% RH. Humidity change step is 5% RH. When the mass change rate dm/dt is less than 0.002%, it is considered as scale balance. Mass change rate less than 0.01%/min within 5 minutes is the balance criterion in the test and the maximum equilibration time is 2 hours. |

Information about materials and reagents used in the invention is as follows:

| Material | Purity/grade | Lot No. | Manufacturer |
|---|---|---|---|
| Compound of formula V | ≥98.0% | KM1009-1804001 | ZINNOVA |
| Compound of formula IV | ≥98.0% | KM1008-1804001 | ZINNOVA |
| N,N-Diisopropylethylamine (DIPEA) | AR | KM261A-1801002 | Shanghai Qiao Chemical Science Co., Ltd. |
| Ethanol | / | 160321047B | Nanjing Chemical Reagent Co., Ltd. |
| Methanol | AR | P1176856 | GENERAL-REAGENT |
| Tetrahydrofuran | AR grade | P1167158 | GENERAL-REAGENT |
| Dichloromethane | AR | P1216848 | GENERAL-REAGENT |
| Ethyl acetate (EA) | AR | P1080359 | GENERAL-REAGENT |
| Acetone | AR | P1160778 | GENERAL-REAGENT |
| Purified water | Milli-Q | Prepared on the same day | Milli-Q |
| Methyl tert-butyl ether | AR | P1135054 | GENERAL-REAGENT |
| Isopropanol | HPLC | 6553IU13 | Anhui Fulltime Specialized Solvent & Reagent Co., Ltd. |
| Palladium on carbon (Pd/C) | AR | KM416A-1603001 | Shaanxi Rock New Materials Co., Ltd. |

| Material | Purity/grade | Lot No. | Manufacturer |
| --- | --- | --- | --- |
| (R)-lactamide | AR | KM1012-1806001 | Shanghai Zhongnai Biological Medical Technology Co., Ltd. |
| Et3O—BF4 | AR | KM416A-1603001 | Shaanxi Rock New Materials Co., Ltd. |
| Hydrochloric acid | AR | GM007-1809001 | Suzhou Zhoushi Chemical Reagent Co., Ltd. |
| Potassium carbonate | Industrial grade | GM009-1804001 | Shanghai Weitang Industry Co., Ltd. |

EXAMPLES

Preparation of a Compound of Formula III

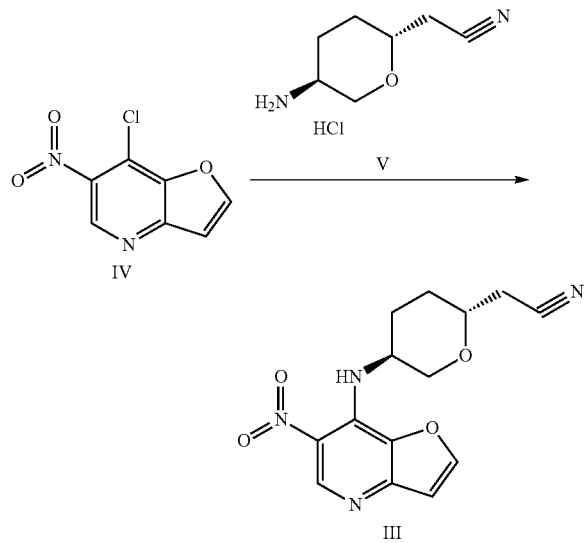

Example 1 Preparation of a Compound of Formula III

Ethanol (4 mL), a compound of formula IV (0.20 g, 1.0 eq), a compound of formula V (0.18 g, 1.0 eq), and DIPEA (0.39 g, 3.0 eq) were added to a 25 mL three-necked flask, then the system was stirred; under nitrogen protection, the system was heated to reflux (70-80° C.), and stirred overnight at the reflux temperature; the system was cooled to room temperature (15-20° C.), solids were precipitated during cooling; water (4 mL) was added to the system dropwise, the system was stirred for 2 hours at room temperature (15-20° C.); then the system was filtered, the filter cake was washed with ethanol solution (2 mL, V/V, 1:1), the filter cake was dried under vacuum at a temperature between 45-50° C. for 16 hours; about 0.21 g of yellow solid was obtained, with a LC-MS purity of 96.4% (214 nm) and a yield of 69%.

MS-ESI: [M+1]+: 303.1

$^1$H NMR (400 MHz, CDCl$_3$): 9.238 (s, 1H), 8.400 (d, 1H), 7.968 (d, 1H), 6.987 (d, 1H), 4.537-4.613 (m, 1H), 4.305-4.350 (m, 1H), 3.661-3.722 (m, 1H), 3.313-3.366 (m, 1H), 2.590-2.699 (m, 2H), 2.407-2.454 (m, 1H), 1.815-2.035 (m, 1H), 1.688-1.806 (m, 2H).

Example 2 Preparation of a Compound of Formula III

Ethanol (120 mL, 20 V), a compound of formula IV (6.0 g, 1.0 eq), a compound of formula V (5.4 g, 1.01 eq) and DIPEA (11.7 g, 3.0 eq) were added to a 250 mL three-necked flask, the system was stirred; under nitrogen protection, the system was heated to 70-80° C. (internal temperature), and the temperature was maintained and the system was stirred for 8 hours; the system was cooled to room temperature (15-20° C.), solids were precipitated during cooling; water (120 mL, 20 V) was added to the system dropwise, the system was stirred for 2 hours at room temperature (10-15° C.); the system was filtered, the filter cake was washed with ethanol solution (30 mL, 1:1); the filter cake was dried under vacuum at 50° C. for 16 hours; about 7.7 g of yellow solid was obtained, with an HPLC purity of 95.5% and a yield of 84.3%.

The MS-ESI and $^1$H NMR data are consistent with example 1.

Example 3 Preparation of a Compound of Formula III

Ethanol (5 mL, 10V), a compound of formula IV (0.50 g, 1.0 eq), a compound of formula V (0.45 g, 1.01 eq), and DIPEA (0.98 g, 3.0 eq) were added to a 25 mL three-necked flask, the system was stirred; under nitrogen protection, the system was heated to 70-80° C., allowed the system to reflux and the system was stirred for 5 hours; the system was cooled to room temperature (15-20° C.), solids were precipitated during cooling; water (5 mL, 10V) was added to the system dropwise, the system was stirred for 2 hours at room temperature (10-15° C.); the system was filtered, the filter cake was washed with ethanol solution (1:1) (1.5 mL, 3V), the filter cake was dried under vacuum at 50° C. for 16 hours; about 0.54 g of brown solid was obtained, with an HPLC purity of 95.4% and a yield of 71%.

The MS-ESI and $^1$H NMR data are consistent with example 1.

Example 4 Preparation of a Compound of Formula III

Ethanol (5 mL, 10V), a compound of formula IV (0.50 g, 1.0 eq), a compound of formula V (0.45 g, 1.01 eq) and DIPEA (0.72 g, 2.2 eq) were added to a 25 mL three-necked flask, the system was stirred; under nitrogen protection, the system was heated to 70-80° C., allowed the system to reflux and the system was stirred for 5 hours; the system was cooled to room temperature (15-20° C.), solids were precipitated during cooling; water (7.5 mL, 15V) was added to the system dropwise, the system was stirred for 1 hour at room temperature (10-15° C.); the system was cooled to

Example 5 Preparation of a Compound of Formula III

Ethanol (50 mL, 10V), a compound of formula IV (5.0 g, 1.0 eq), a compound of formula V (4.5 g, 1.01 eq) and DIPEA (7.2 g, 2.2 eq) were added to a 250 mL three-necked flask, the system was stirred; under nitrogen protection, the system was heated to 70-80° C., allowed the system to reflux and the system was stirred for 5 hours; the system was cooled to room temperature (15-20° C.), solids were precipitated during cooling; water (75 mL, 15V) was added to the system dropwise, the system was stirred for 1 hour at room temperature (10-15° C.); the system was cooled to 5-10° C. and was stirred for 2 hours; the system was filtered, the filter cake was washed with ethanol solution (1:1, 15 mL), the filter cake was dried under vacuum at 50° C. for 16 hours; about 6.6 g of yellow solid was obtained, with an HPLC purity of 94.2% and a yield of 86.7%.

The MS-ESI and $^1$H NMR data are consistent with example 1.

Example 6 Preparation of a Compound of Formula III

Ethanol (180 mL, 10V), a compound of formula IV (17.8 g, 1.0 eq), a compound of formula V (16.0 g, 1.01 eq), and DIPEA (25.7 g, 2.2 eq) were added to a 500 mL three-necked flask, the system was stirred; under nitrogen protection, the system was heated to 70-80° C., allowed the system to reflux and the system was stirred for 5 hours; the system was cooled to room temperature (15-20° C.), solids were precipitated during cooling; water (270 mL, 15V) was added to the system dropwise, the system was stirred for 1 hour at room temperature (10-15° C.); the system was cooled to 5-10° C. and was stirred for 2 hours; the system was filtered, the filter cake was washed with ethanol solution (ethanol:water=1:1.5, v/v, 40 mL), the filter cake was dried under vacuum at 50° C. for 16 hours; about 23.0 g of brown solid was obtained, with an HPLC purity of 95.3% and a yield of 85.2%.

The MS-ESI and $^1$H NMR data are consistent with example 1.

Example 7 Preparation of a Compound of Formula III

Ethanol (1000 mL, 10V), a compound of formula IV (100 g, 1.0 eq), a compound of formula V (89.9 g, 1.01 eq), and DIPEA (143.2 g, 2.2 eq) were added to a 3000 mL three-necked flask, the system was stirred; under nitrogen protection, the system was heated to 85-90° C. (internal temperature, about 75° C.), allowed the system to reflux and the system was stirred for 10 hours; the system was cooled to room temperature (15-20° C.), solids were precipitated during cooling; water (1500 mL, 15V) was added to the system dropwise, the system was stirred for 1 hour at room temperature (10-15° C.); the system was cooled to 5-10° C. and was stirred for 2 hours; the system was filtered, the filter cake was washed with ethanol solution (1:1.5, v/v, 200 mL), the filter cake was dried with an air blower at 50° C. for 16 hours; about 130 g of reddish brown solid was obtained, with an HPLC purity of 94.2% and a yield of 85.5%.

The MS-ESI and $^1$H NMR data are consistent with example 1.

Example 8 Preparation of a Compound of Formula III

Ethanol (2000 mL, 10V), a compound of formula IV (200 g, 1.0 eq), a compound of formula V (179.7 g, 1.01 eq), and DIPEA (286.4 g, 2.2 eq) were added to a 5000 mL three-necked flask, the system was stirred; under nitrogen protection, the system was heated to 70-80° C. (internal temperature, about 65-70° C.), allowed the system to reflux and the system was stirred for 16 hours; the system was cooled to room temperature (15-20° C.), solids were precipitated during cooling; water (3000 mL, 15V) was added to the system dropwise, the system was stirred for 1 hour at room temperature (10-15° C.); the system was cooled to 5-10° C. and was stirred for 2 hours; the system was filtered, the filter cake was washed with ethanol solution (1:1.5, v/v, 400 mL), the filter cake was dried with an air blower at 50° C. for 16 hours; about 251 g of reddish brown solid was obtained, with an HPLC purity of 93.4% and a yield of 78.1%.

The MS-ESI and $^1$H NMR data are consistent with example 1.

Example 9 Preparation of a Compound of Formula III

Ethanol (5000 mL, 10V), a compound of formula IV (500 g, 1.0 eq), a compound of formula V (450 g, 1.01 eq), and DIPEA (723 g, 2.2 eq) were added to a 20000 mL three-necked flask, the system was stirred; under nitrogen protection, the system was heated to 80-90° C. (internal temperature, about 70-80° C.), allowed the system to reflux and the system was stirred for 16 hours; the system was cooled to room temperature (25-30° C.), solids were precipitated during cooling; water (7500 mL, 15V) was added to the system dropwise, the system was stirred for 1 hour at room temperature (25-30° C.); the system was cooled to 10-15° C. and was stirred for 2 hours; the system was filtered, the filter cake was washed with ethanol solution (1:1.5, v/v, 1000 mL), the filter cake was dried in an at 50-55° C. under vacuum for 24 hours; about 623 g of product was obtained, with an HPLC purity of 93.7%, residual ethanol of 0.5%, a content of 93.1%, and a content yield of 76.2%.

The MS-ESI and $^1$H NMR data are consistent with example 1.

Example 10 Preparation of a Compound of Formula III

Ethanol (100 mL, 10V), a compound of formula IV (10.0 g, 1.0 eq), a compound of formula V (9.0 g, 1.01 eq), and DIPEA (14.3 g, 2.2 eq) were added to a 500 mL three-necked flask, the system was stirred; the system was heated to 70-80° C., allowed the system to reflux and the system was stirred for 16 hours; the system was cooled to room temperature (20-30° C.), solids were precipitated during cooling; water (150 mL, 15V) was added to the system dropwise, the system was stirred for 2 hours at room temperature (20-30° C.); the system was cooled to 5-10° C. and was stirred for 2 hours; the system was filtered, the filter cake was washed with ethanol solution (1:1.5, v/v, 25 mL), the filter cake was dried in an oven at 50-55° C. under vacuum for 16 hours; about 13.7 g of product was obtained, with an HPLC purity of 93.7% and a yield of 90%.

The MS-ESI and $^1$H NMR data are consistent with example 1.

Example 11 Preparation of a Compound of Formula III

Ethanol (17 kg, 10V), a compound of formula IV (2.2 Kg, 1.0 eq), a compound of formula V (1.98 Kg, 1.01 eq), and DIPEA (3.19 Kg, 2.2 eq) were added to a R0462 reactor, the system was stirred; under nitrogen protection, the system was heated to 75-80° C. (internal temperature, about 70-80° C.), the system was stirred for 16 hours; the system was cooled to room temperature (15-25° C.), solids were precipitated during cooling; water (33 Kg, 15V) was added to the system dropwise, the system was stirred for 2 hours at room temperature (10-15° C.); the system was cooled to 5-10° C. and was stirred for 4 hours; the system was filtered, the filter cake was washed with ethanol solution (ethanol:water=1:2, v/v, 6.2 Kg), the filter cake was dried under the vacuum condition of ≤−0.08 MPa in a jacket at 45-55° C. for 16 hours; 2.64 Kg of brown solid was obtained, with an HPLC purity of 94.0%, a content of 93.4%, and a content yield of 79.04%.

The MS-ESI and $^1$H NMR data are consistent with example 1.

Preparation of a Compound of Formula II

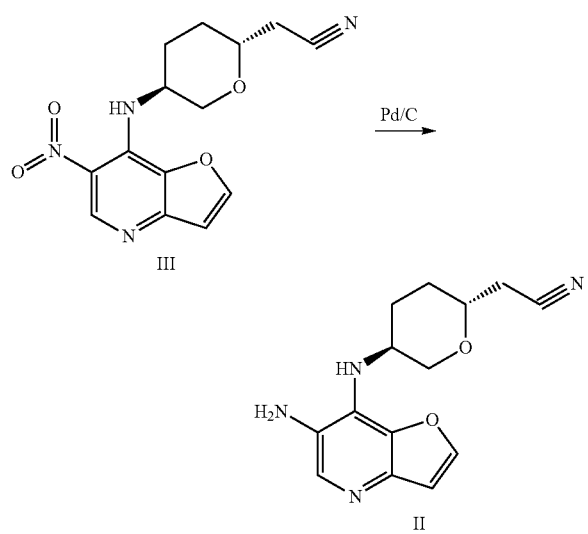

Example 12 Preparation of a Compound of Formula II

A compound of formula III (5.0 g), THF (50 mL, 10 V) and palladium on carbon (0.75 g, 10% Pd/C, 50% water wet) were added to a 100 mL stainless steel high pressure reactor successively; the system was purged with nitrogen for 5 times and then hydrogen for 5 times; the pressure of system was increased to 0.50 MPa with hydrogen, and the system was heated to 25-35° C. and the temperature was maintained, the system was stirred for 24 hours; the reaction solution was filtered with diatomite, the filter cake was washed with THF (20 mL), the filtrate was concentrated to dryness, 4.2 g of brown solid was obtained, with an HPLC purity of 94.9% and a yield of 93.3%.

MS-ESI: [M+1]+: 273.1
$^1$H NMR (400 MHz, CDCl$_3$): 7.988 (s, 1H), 7.688 (d, 1H), 6.805 (d, 1H), 4.190-4.338 (m, 3H), 3.584-3.648 (m, 1H), 3.147-3.206 (t, 1H), 2.594-2.651 (d, 2H), 2.318-2.364 (m, 1H), 1.917-1.974 (m, 1H), 1.633-1.738 (m, 1H), 1.456-1.525 (m, 1H).

Example 13 Preparation of a Compound of Formula II

A compound of formula III (120.0 g), THF (2400 mL, 20 V) and palladium on carbon (18 g, 10% Pd/C, 50% water wet) were added to a 5000 mL stainless steel high pressure reactor successively; the system was purged with nitrogen for 5 times and then hydrogen for 5 times; the pressure of system was increased to 0.50 MPa with hydrogen, and the system was heated to 25-35° C. and the temperature was maintained, the system was stirred for 24 hours; the reaction solution was filtered with diatomite, the filter cake was washed with THF (600 mL) (until TLC almost does not show fluorescence), the filtrate was concentrated to obtain 130 g of black semi-oily solid, with an HPLC purity of 91.7% and a yield of 120.26%. an HPLC purity The MS-ESI and $^1$H NMR data are consistent with example 12.

Example 14 Preparation of a Compound of Formula II

A compound of formula III (100.0 g), THF (2000 mL, 20 V) and palladium on carbon (15.0 g, 10% Pd/C, 50% water wet) were added to a 5 L stainless steel high pressure reactor successively; the system was purged with nitrogen for 5 times and then hydrogen for 5 times; the pressure of system was increased to 0.5-1.0 MPa with hydrogen, the temperature of the jacket was set at 30° C. and the system was stirred for 16 hours with the temperature maintained, the reaction solution was filtered with diatomite, the filter cake was washed with THF (1000 mL), 3877 g of a compound of formula II in THF was obtained. Post-treatment 1: the above filtrate (1820 g, about 40 g of a compound of formula II calculated according to a 100% yield) was concentrated to (2-3 V, 80-120 mL) with rotary evaporator, the system was exchanged with ethanol (150 mL×2) to (2-3 V, 80-120 mL); 78 g of a compound of formula II in ethanol was obtained, with a content of 47.25%, content yield of 92.14%.

Post-treatment 2: the above filtrate (450 g, about 10 g of a compound of formula II calculated according to a 100% yield) was concentrated to dryness with rotary evaporator; 10.5 g of brownish red solid was obtained.

Post-treatment 3: the above filtrate (450 g, about 10 g of a compound of formula II after calculation) was placed in a flask, and was concentrated to about 30-40 mL (3-4 V) with rotary evaporator; the concentrate residue was exchanged with ethanol (50 mL×2) to about 30-40 mL (3-4 V); black oily concentrate residue was obtained, the concentrate residue was directly fed to the next step of reaction.

The MS-ESI and $^1$H NMR data are consistent with example 12.

Example 15 Preparation of a Compound of Formula II

THF (240 mL, 20 V), a compound of formula III (12.0 g), and palladium on carbon (1.8 g, 5% Pd/C, 50% water wet) were added to a 500 mL three-necked flask successively; the system was purged with nitrogen for 5 times and then hydrogen for 5 times; the system was stirred for 48 hours with the temperature maintained at room temperature (25-30° C.) and a hydrogen pressure (about 0.1 MPa); the reaction solution was filtered, the filter cake was washed with THF (60 mL), the combined filtrate was concentrated to 20-30 mL with a rotary evaporator, then was exchanged with ethanol (60 mL×2) to 20-30 mL; 24 g of a compound of formula II in ethanol was obtained, the solution was used directly for the next step of reaction.

The MS-ESI and $^1$H NMR data are consistent with example 12.

Example 16 Preparation of a Compound of Formula II

THF (1500 mL, 15 V), a compound of formula III (100 g), and palladium on carbon (15 g, 5% Pd/C, 50% water wet) were added to a 5000 mL three-necked flask successively; the system was purged with nitrogen for 5 times and then hydrogen for 5 times; the system was stirred for 48 hours with the temperature maintained at room temperature (20-25° C.) and a hydrogen pressure (about 0.1 MPa); the reaction solution was filtered, the filter cake was washed with THF (200 mL), the combined filtrate was concentrated to 200-300 mL with a rotary evaporator; 185.6 g of a compound of formula II in THF was obtained, with an HPLC purity of 94.2%, a content of 43.2%, and a content yield of 94.0%.

The MS-ESI and $^1$H NMR data are consistent with example 12.

Example 17 Preparation of a Compound of Formula II

THF (12400 mL, 20 V), a compound of formula III (620 g), and palladium on carbon (93 g, 5% Pd/C, 50% water wet) were added to a 20000 mL three-necked flask successively; the system was purged with nitrogen for 5 times and then hydrogen for 5 times; the system was stirred for 48 hours with the temperature maintained at room temperature (30-35° C.) and a hydrogen pressure (about 0.1 MPa); the reaction solution was filtered with diatomite (200 g), the filter cake was washed with THF (1200 mL), the combined filtrate was concentrated to 1200-1800 mL with a rotary evaporator; 1664 g of a compound of formula II in THF was obtained, with an HPLC purity of 93.8%, a content of 34.57%, and a content yield of 110.6%.

The MS-ESI and $^1$H NMR data are consistent with example 12.

Example 18 Preparation of a Compound of Formula II

THF (140 ml, 70 V), a compound of formula III (2.0 g) and palladium on carbon (0.3 g, 5% Pd/C, 50% water wet) were added to a 250 mL high pressure reactor; the high pressure reactor was covered and the nut was screwed tight; the system was purged with nitrogen for 3 times and then hydrogen for 3 times; the high pressure reactor was charged with hydrogen to about a pressure of 0.50±0.05 MPa, the inlet valve was then closed; the stirring apparatus was started at a rotating speed of 500 r/min; hydrogen pressure in the high pressure reactor was maintained at 0.5±0.05 MPa between 25-35° C., the high pressure reactor was stirred and the system was reacted for 96 hours; the reaction solution was filtered with diatomite (10 g), the filter cake was washed with THF (60 mL); the combined filtrate was concentrated with rotary evaporator to dryness to obtain 1.8 g of semi-oily solid, with an HPLC purity of 91.2%, a yield of 99.9%.

The MS-ESI and $^1$H NMR data are consistent with example 12.

Example 19 Preparation of a Compound of Formula II

THF (167 Kg, 70 V), a compound of formula III (2.64 Kg) and palladium on carbon (0.4 Kg, 5% Pd/C, 50% water wet) were added to a 500 L high pressure reactor; the system was purged with nitrogen for 5 times and then hydrogen for 5 times; the high pressure reactor was charged with hydrogen to about a pressure of 0.50±0.05 MPa, the inlet valve was then closed; the stirring apparatus was started; hydrogen pressure in the high pressure reactor was maintained at 0.5±0.05 MPa between 25-35° C., the high pressure reactor was stirred and the system was reacted for 120 hours; the reaction solution was filter-pressed, the filter cake was washed with THF (13 Kg); the combined filtrate was distillated under reduced pressure (to 2V-3V) to obtain 11 Kg of a compound of formula II in THF, with an HPLC purity of 90.7%, a content of 18.5%, and a content yield of 91.9%.

The MS-ESI and $^1$H NMR data are consistent with example 12.

Example 20 Preparation of a Compound of Formula II

THF (60 mL, 12 V), a compound of formula III (5.0 g) and palladium on carbon (0.75 g, 5% Pd/C, 50% water wet) were added to a 100 mL stainless steel high pressure reactor; the system was purged with nitrogen for 5 times and then hydrogen for 5 times; the high pressure reactor was charged with hydrogen to about a pressure of 0.5-1.0 MPa, the jacket temperature was set to 30° C., and the system was stirred for 42 hours with the temperature maintained; after the reaction was completed, the reaction solution was filtered with diatomite, the filter cake was washed with THF (100 mL); 197.8 g of a compound of formula II in THF was obtained; the solution was concentrated with a rotary evaporator to (2-3 V, 10-15 mL); the system was exchanged with ethanol (25 mL×2) to (2-3 V, 10-15 mL); the obtained compound of formula II in ethanol was directly used for the next step of reaction.

The MS-ESI and $^1$H NMR data are consistent with example 12.

Preparation of a Compound of Formula I

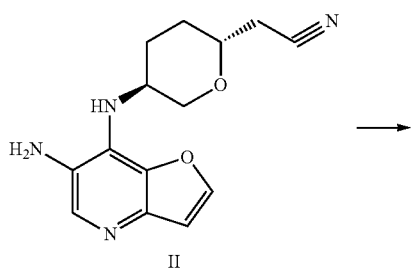

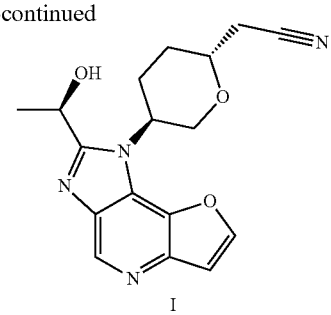

I

Example 21 Preparation of a Compound of Formula I

THF (60 mL, 12 V), (R)-lactamide (6.6 g, 4.0 eq) and Et₃O—BF₄ (13.9 g, 4.0 eq) were added to a 250 mL three-necked flask #1, the system was stirred; the materials in three-necked flask #1 were stirred under nitrogen protection for later use; a compound of formula II (5.0 g, 1.0 eq) and ethanol (80 mL, 16 V) were added to another 250 mL three-necked flask #2; the system was heated to 70±5° C. under nitrogen protection; the materials in three-necked flask #1 were added to three-necked flask #2 with a syringe dropwise within 10-20 minutes; the system was heated to 85±5° C. (internal temperature was in the range of 72-75° C.) under nitrogen protection for reacting for 2 hours; the system was cooled to room temperature; the reaction liquid was concentrated with a rotary evaporator until there was basically no fraction flowing out; 1M HCl (80 mL) was added to the residual concentrated liquid, the pH was about 1 (determined with a pH test paper); the system was extracted four times with DCM (50 mL×4); the pH of the aqueous phase was adjusted to 7-8 with saturated sodium bicarbonate solution; the system was stirred at room temperature for 0.5 hour, then was filtered, the filter cake was washed with water (60 mL) and EA (10 mL), respectively; the filter cake was dried under vacuum at 50° C. for 16 hours; 4.3 g of faint yellow solid was obtained, with a purity of 95.0%; the solid was dissolved with methanol (30 mL); 4.1 g of silicon based metal eliminator and 1.0 g of activated carbon were added, the system was heated to 50° C. and stirred for 1 hour, then was cooled, filtered, washed with methanol (30 mL); the filtrate was concentrated with rotary evaporator until there was basically no fraction flowing out; methanol (10 mL) and MTBE (25 mL) were added to the residue, the system was heated to 50° C., and was stirred for 0.5 hour, then was cooled, the system was cooled to 10±5° C. and stirred for 0.5 hour; filtered, the filter cake was washed with MTBE (25 mL); the filter cake was dried under vacuum at 50° C. for 16 hours, 3.2 g of faint yellow solid was obtained, with a purity of 97.9%.

MS-ESI: [M+1]+: 327.6

¹H NMR (400 MHz, CDCl₃): 8.988 (s, 1H), 7.922 (d, 1H), 7.175 (d, 1H), 5.200-5.265 (m, 1H), 4.859-4.942 (m, 1H), 4.350-4.406 (t, 1H), 4.020-4.108 (m, 2H), 3.067 (d, 1H), 2.619-2.779 (m, 3H), 2.108-2.269 (m, 2H), 1.790-1.895 (m, 3H).

Example 22 Preparation of a Compound of Formula I

THF (650 mL, 12 V), (R)-lactamide (70.6 g, 4.0 eq) and Et₃O—BF₄ (150.6 g, 4.0 eq) were added to a 1000 mL three-necked flask #1, the system was stirred; the materials in three-necked flask #1 were stirred under nitrogen protection for later use; a compound of formula II (54 g, 1.0 eq) and ethanol (860 mL, 16 V) were added to another 2000 mL three-necked flask #2; the system was heated to 70±5° C. under nitrogen protection; the materials in three-necked flask #1 were slowly added to three-necked flask #2 dropwise within 1 hour; the system was heated to 85±5° C. (internal temperature was in the range of 72-75° C.) under nitrogen protection for reacting for 2 hours; the system was cooled to room temperature; the reaction liquid was concentrated with a rotary evaporator until there was basically no fraction flowing out; 1M HCl (450 mL) was added to the residual concentrated liquid, the pH was about 1 (determined with a pH test paper); the system was extracted four times with DCM (270 mL×4); the pH of the aqueous phase was adjusted to 7-8 with saturated sodium bicarbonate solution; the system was stirred at room temperature for 0.5 hour, then was filtered, the filter cake was washed with water (540 mL); MTBE (270 mL) was added to the filter cake, the system was stirred at room temperature for 0.5 hour, filtered, the filter cake was washed with MTBE (108 mL); the filter cake was dried under vacuum at 50° C. for 16 hours; 49.2 g of light yellow solid was obtained, with an HPLC purity of 94.2%; the solid was dissolved with methanol (380 mL); silicon based metal eliminator (44 g) and activated carbon (5.4 g) were added, the system was heated to 50° C. and stirred for 1 hour, then was cooled, filtered, washed with methanol (430 mL); the filtrate was concentrated with a rotary evaporator to (80-110 mL, 1.5 V-2 V); MTBE (540 mL) was added to the residue, the system was heated to 50° C., and was stirred for 1 hour, then was cooled to 10±5° C. and stirred for 0.5 hour; filtered, the filter cake was washed with MTBE (270 mL); 42.4 g of filter cake was obtained, with an HPLC purity of 96.9%; the filter cake was dried under vacuum at 50° C. for 16 hours, 41.0 g of light yellow solid was obtained, with an HPLC purity of 96.7%, a yield of 63.3%.

Purification of a Compound of Formula I:

A compound of formula I (41 g) was dissolved with methanol; silica gel (50 g) was added to the solution, the system was concentrated to dryness for later use; silica gel (200 g) was added to the chromatographic column, the column was compacted with an air pump; a compound of formula I mixed with silica gel was added to the chromatographic column, the column was compacted with an air pump; the chromatographic column was eluted with an eluent ($V_{MeOH}$:$V_{DCM}$=1:100-1:30); qualified components were collected, concentrated to dryness; the product was dried under vacuum at 50° C. for 16 hours; 36 g of off-white solid was obtained, with an HPLC purity of 98.5%.

The MS-ESI and ¹H NMR data are consistent with example 21.

Example 23 Preparation of a Compound of Formula I

THF (60 mL, 6 V), (R)-lactamide (13.2 g, 4.0 eq) and Et₃O—BF₄ (27.9 g, 4.0 eq) were added to a 100 mL three-necked flask #1, the system was stirred; the materials in #1 were stirred under nitrogen protection for later use; a compound of formula II (10 g, 1.0 eq) and ethanol (100 mL, 10 V) were added to another 250 mL three-necked flask #2; the system was heated to 70±5° C. under nitrogen protection; the materials in three-necked flask #1 were slowly added to three-necked flask #2 dropwise within 20 minutes; the system was heated to 80±5° C. (internal temperature was in the range of 72-75° C.) under nitrogen protection for reacting for 0.5 hour; the system was cooled to room temperature 20-30° C.; the reaction liquid was concentrated to about 50-80 mL with a rotary evaporator between 30-40° C.; water (100 mL, 10 V) was added to the system, then the system was concentrated with a rotary evaporator between 30-40° C. until there was basically no fraction flowing out; the system was cooled to 20-30° C.; the temperature of the system was controlled at 20-30° C., 12M HCl (5.5 g) was used to adjust the pH of the system to 2-3, the system was extracted with ethyl acetate (50 mL×2, 5V×2); the organic phase was discarded, and the aqueous phase was transferred to a flask; the temperature of the system was controlled at 20-30° C., the pH of the system was adjusted to 8-9 with saturated potassium carbonate solution (23 g); the temperature of the system was controlled at 20-25° C., the system was stirred for 2 hours, then was filtered, the filter cake was washed with water (50 mL) and MTBE (50 mL); the filter cake was dried with an air blower at 50° C. for 24 hours, 18 g of earth yellow solid was obtained, with an HPLC purity of 93.5%.

The MS-ESI and $^1$H NMR data are consistent with example 21.

Example 24 Preparation of a Compound of Formula I

THF (120 mL, 12 V), (R)-lactamide (13.2 g, 4.0 eq) and Et$_3$O—BF$_4$ (27.8 g, 4.0 eq) were added to a 250 mL three-necked flask #1, the system was stirred; the materials in #1 were stirred under nitrogen protection for later use; a compound of formula II (10 g, 1.0 eq) and ethanol (140 mL, 14 V) were added to another 500 mL three-necked flask #2; the system was heated to 40-45° C. (internal temperature) under nitrogen protection; the materials in three-necked flask #1 were added to three-necked flask #2 dropwise within 1 hour; the system was maintained at 40-45° C. (internal temperature) under nitrogen protection for reacting for 4.5 hours; the system was cooled to room temperature, and water (20 mL, 2V) was added; the system was concentrated with a rotary evaporator at 30-40° C. until there was basically no fraction flowing out; the system was cooled to 20-30° C.; the temperature of the system was controlled at 20-30° C., 12M HCl (3 mL) was used to adjust the pH of the system to 2-3, the system was extracted with ethyl acetate (50 mL×2, 5V×2); the organic phase was discarded, and the aqueous phase was transferred to a flask; the temperature of the system was controlled at 20-30° C., the pH of the system was adjusted to 8-9 with 50% potassium carbonate solution (15 mL); the temperature of the system was controlled at 20-25° C., the system was stirred for 2 hours, then was filtered, the filter cake was washed with water (50 mL) and acetone (50 mL); the crude product was triturated and stirred with water (50 mL) at 20-25° C. for 1 hour; the system was filtered, the filter cake was washed with water (50 mL) and acetone (50 mL); the filter cake was dried with an air blower at 50° C. for 24 hours, 17.8 g of khaki solid was obtained, with an HPLC purity of 95.3%.

The MS-ESI and $^1$H NMR data are consistent with example 21.

Example 25 Preparation of a Compound of Formula I

THF (60 mL, 12 V), (R)-lactamide (6.6 g, 4.0 eq) and Et$_3$O—BF$_4$ (13.9 g, 4.0 eq) were added to a 250 mL three-necked flask #1, the system was stirred; the materials in three-necked flask #1 were stirred under nitrogen protection for later use; a compound of formula II (5 g, 1.0 eq) and ethanol (70 mL, 14 V) were added to another 250 mL three-necked flask #2; the system was heated to 40-45° C. (internal temperature) under nitrogen protection; the materials in three-necked flask #1 were added to three-necked flask #2 dropwise within 20 minutes; the system was maintained at 40-45° C. (internal temperature) under nitrogen protection for reacting for 3 hours; the system was cooled to room temperature and was filtered, the filter cake was washed with THF (10 mL); water (10 mL, 2V) was added to the filtrate; the filtrate was concentrated with a rotary evaporator to 10-20 mL (2V-4V), the concentrated residue was exchanged with ethyl acetate (25 mL×2) and concentrated to 10-20 mL (2V-4V); water (50 mL, 10V) was added to the concentrated residue; the internal temperature was controlled at 20-25° C., 12M HCl (4.1 g) was used to adjust the pH of the system to 1-2; activated carbon (0.5 g) was added to the system, and the system was stirred at room temperature for 2 hours, and was filtered, the filter cake was washed with water (10 mL) and 1M HCl (10 mL); the combined filtrate was extracted with ethyl acetate (25 mL×2), the organic phase was discarded; the internal temperature was controlled at 20-25° C., the pH of the system was adjusted to 9-10 with saturated potassium carbonate solution (15 g); the internal temperature was controlled at 15-20° C., the system was stirred for 1 hour, and was filtered, the filter cake was washed with water (10 mL); the filter cake was triturated with acetone aqueous solution (50 mL, V/V=1:1) for 1 hour; the system was filtered, the filter cake was washed with acetone aqueous solution (10 mL, V/V=1:1); the filter cake was dried with an air blower at 50° C. for 24 hours; 5.0 g of pale gray solid was obtained, with an HPLC purity of 95.6%, and a yield of 83.5%;

Purification of a Compound of Formula I:

5.0 g of the obtained solid and methanol (40 mL) were added to a flask, and were stirred for 10 minutes at room temperature, the materials were basically dissolved and the solution was clear; activated carbon (0.5 g) and silica gel (4.0 g) were added to the system; the system was heated to 50-55° C., the temperature was maintained and the system was stirred for 2 hours, then was filtered with silica gel (5 g), the filter cake was washed with methanol (50 mL); the filtrate was concentrated with a rotary evaporator to 5-10 mL; MTBE (50 mL) was added to the concentrated residue; the system was heated to reflux, and was allowed for reflux for 1 hour; the system was cooled to 5-10° C., the temperature was maintained and the system was stirred for 1 hour and was filtered, the filter cake was washed with MTBE; the filter cake was dried with a drying oven under vacuum at 50° C. for 16 hours; 3.0 g of off-white solid was obtained, with a yield of 60% and a purity of 97.9%; the filtrate was concentrated to dryness to obtain 1.4 g of yellow solid.

The MS-ESI and $^1$H NMR data are consistent with example 21.

Example 26 Preparation of a Compound of Formula I

THF (55 mL, 12 V), (R)-lactamide (5.9 g, 4.0 eq) and Et$_3$O—BF$_4$ (12.6 g, 4.0 eq) were added to a 250 mL three-necked flask #1, the system was stirred; the materials in #1 were stirred under nitrogen protection for later use; a compound of formula II (4.5 g, which is 5.0 g of a compound of formula III in example 20 calculated according to a yield of 100%) and ethanol (70 mL, 15.5 V) were added to another 250 mL three-necked flask #2; the system was heated to reflux under nitrogen protection; the materials in three-necked flask #1 were dropwise added to three-necked flask #2 at one time; under nitrogen protection, the system was heated to 85±5° C. (internal temperature 74-76° C.) for reacting for 1 hour; the system was cooled to room temperature and was filtered, the filter cake was washed with THF (10 mL); water (10 mL, 2V) was added to the filtrate; the filtrate was concentrated with a rotary evaporator to 10-20 mL (2V-4V), the concentrated residue was exchanged with ethyl acetate (25 mL×2) and concentrated to 10-20 mL (2V-4V); water (50 mL, 10V) was added to the concentrated residue; the internal temperature was controlled at 20-25° C., 12M HCl (3.6 g) was used to adjust the pH of the system to 1-2; activated carbon (0.5 g) was added to the system, and the system was stirred at room temperature for 2 hours, and was filtered, the filter cake was washed with water (10 mL) and 1M HCl (10 mL); the combined filtrate was extracted with ethyl acetate (25 mL×2), the organic phase was discarded; the internal temperature was controlled at 20-25° C., the pH of the system was adjusted to 9-10 with saturated potassium carbonate solution (15 g); the internal temperature was controlled at 15-20° C., the system was stirred for 1 hour, and was filtered, the filter cake was washed with water (10 mL); the filter cake was triturated with acetone aqueous solution (50 mL, V/V=1:1) for 1 hour; the system was filtered, the filter cake was washed with acetone aqueous solution (10 mL, V/V=1:1); the filter cake was dried with an air blower at 50° C. for 16 hours; 4.9 g of pale gray solid was obtained, with an HPLC purity of 94.5%;

Purification of a Compound of Formula I:

The obtained solid (4.9 g) and ethanol (100 mL) were added to a flask, and were stirred at room temperature for 10 minutes, the materials were basically dissolved and the solution was clear; silica gel (5.0 g, 1×) was added to the system, the system was concentrated with a rotary evaporator to dryness for later use; the crude compound of formula I mixed with silica gel was allowed to pass a silica gel column (40 g, 8×), the column was eluted with a mixed solution of ethyl acetate and ethanol ($V_{EA}:V_{EtOH}$=100:1-30:1); the components were tested with TLC, components containing the product were collected and concentrated to dryness; 0.5 g of white product was obtained with a purity of 95.0% and 2.9 g of faint yellow product was obtained with a purity of 98.7%; ethyl acetate (30 mL) and ethanol (3 mL) were added to a flask containing 2.9 g of the product; the system was heated to reflux, and allowed the system to reflux for 1 hour; the system was cooled to 5-10° C., the temperature was maintained and the system was stirred for 1 hour, and was filtered, the filter cake was washed with ethyl acetate (5 mL); the filter cake was dried with a drying oven under vacuum at 50° C. for 16 hours; 2.3 g of faint yellow to off-white solid was obtained, with an HPLC purity of 99.6%. There were no impurities >0.1%. The total yield of steps 2 and 3 was 42.7%.

The MS-ESI and $^1$H NMR data are consistent with example 21.

Example 27 Preparation of a Compound of Formula I

THF (120 mL, 12 V), (R)-lactamide (13.2 g, 4.0 eq) and Et$_3$O—BF$_4$ (27.8 g, 4.0 eq) were added to a 250 mL three-necked flask #1, the system was stirred; the materials in #1 were stirred under nitrogen protection for later use; ethanol (140 mL, 14V) and the concentrated residue (containing about 10 g of a compound of formula II) obtained after post-treatment 3 in example 14 was added to another 500 mL three-necked flask #2; the system was heated to 45±2° C. under nitrogen protection; the materials in three-necked flask #1 were dropwise added to three-necked flask #2 at one time; under nitrogen protection, the system was heated to 45±5° C. (internal temperature 45° C.) for reacting for 6 hours; the system was cooled to room temperature and was filtered, the filter cake was washed with THF (20 mL); water (20 mL, 2V) was added to the filtrate; the filtrate was concentrated with a rotary evaporator to 20-40 mL (2V-4V), the concentrated residue was exchanged with ethyl acetate (50 mL×2) and concentrated to 20-40 mL (2V-4V); water (90 mL, 10V) was added to the concentrated residue; the internal temperature was controlled at 20-25° C., 12M HCl (8.0 g) was used to adjust the pH of the system to 1-2; activated carbon (1.0 g) was added to the system, and the system was stirred at room temperature for 2 hours, and was filtered, the filter cake was washed with water (20 mL) and 1M HCl (20 mL); the combined filtrate was extracted with ethyl acetate (50 mL×2), the organic phase was discarded; the internal temperature was controlled at 20-25° C., the pH of the system was adjusted to 9-10 with saturated potassium carbonate solution (28 g); the internal temperature was controlled at 15-20° C., the system was stirred for 1 hour, and was filtered, the filter cake was washed with water (20 mL); the filter cake was triturated with acetone aqueous solution (100 mL, V/V=1:1) for 1 hour; the system was filtered, the filter cake was washed with acetone aqueous solution (10 mL, V/V=1:1); the filter cake was dried with an air blower at 50° C. for 16 hours; 15.0 g of pale gray solid was obtained, with a purity of 92.4%.

Purification of a Compound of Formula I:

The obtained solid (10 g) and ethanol (100 mL) were added to a flask; the system was heated to 50-60° C., and stirred at 50-60° C. for 30 minutes, the materials were basically dissolved and the solution was clear; silica gel (20.0 g, 2×) was added to the system, the system was concentrated with a rotary evaporator to dryness for later use; the crude compound of formula I mixed with silica gel was allowed to pass a silica gel column (100 g, 10×), the column was eluted with ethyl acetate until there was basically no former impurities (about 1.5 L), then was eluted with a mixed solution of ethyl acetate and ethanol ($V_{EA}:V_{EtOH}$=100:1-30:1, first 0.5 L of $V_{EA}:V_{EtOH}$=100:1, then 1.5 L of $V_{EA}:V_{EtOH}$=30:1); the components were tested with TLC, components containing the product were collected; qualified components were concentrated by rotary evaporation to (50 mL, 5V); the solvent was exchanged with ethyl acetate (50 mL×2) to (50 mL, 5V); the system was cooled to 5-10° C., and was stirred for 2 hours between 5-10° C.; filtered, the filter cake was washed with ethyl acetate (5 mL); the mother liquid was concentrated to dryness to obtain 0.6 g of product; the filter cake was dried with a drying oven under vacuum at 50° C. for 16 hours; 4.6 g of off-white solid was obtained, with a purity of 98.1%. The total yield of steps 2 and 3 was 57.6%.

The MS-ESI and $^1$H NMR data are consistent with example 21.

Example 28 Preparation of a Compound of Formula I

THF (660 mL, 12 V), (R)-lactamide (72 g, 4.0 eq) and Et$_3$O—BF$_4$ (153.5 g, 4.0 eq) were added to a 1000 mL three-necked flask #1, the system was stirred; the materials in #1 were stirred under nitrogen protection for later use; the compound of formula II in THF prepared in example 16 (127.3 g, 55 g of a compound of formula II after calculation)

was added to a flask, the system was exchanged with EtOH (280 mL×2) and concentrated to 120-180 mL, the concentrated residue was transferred to a 2000 mL three-necked flask #2, and ethanol (770 mL, 14 V) was added, under nitrogen protection, the system was heated to 45-50° C. (internal temperature); the materials in three-necked flask #1 were added to three-necked flask #2 dropwise within about 1 hour; under nitrogen protection, the temperature was maintained at 45-50° C. (basically at about 45° C.) for reacting for 3 hours; the system was cooled to room temperature and was filtered, the filter cake was washed with THF (60 mL); water (110 mL, 2V) was added to the filtrate; the filtrate was concentrated with a rotary evaporator to 110-220 mL (2V-4V), the concentrated residue was exchanged with ethyl acetate (280 mL×2) and concentrated to 110-220 mL (2V-4V); water (550 mL, 10V) was added to the concentrated residue; the internal temperature was controlled at 20-25° C., 12M HCl (35 g) was used to adjust the pH of the system to 1-2; activated carbon (5.5 g) was added to the system, and the system was stirred at room temperature for 2 hours, and was filtered, the filter cake was washed with water (110 mL) and 1M HCl (10 mL); the combined filtrate was extracted with ethyl acetate (280 mL×2), the organic phase was discarded; the internal temperature was controlled at 20-25° C., the pH of the system was adjusted to 9-10 with 50% potassium carbonate solution (180 g); the internal temperature was controlled at 15-20° C., the system was stirred for 2 hours, and was filtered, the filter cake was washed with water (110 mL); the filter cake was triturated with acetone aqueous solution (550 mL, V/V=1:1) for 2 hours; the system was filtered, the filter cake was washed with acetone aqueous solution (110 mL, V/V=1:1); the filter cake was dried with an air blower at 50° C. for 16 hours; 80 g of pale gray solid was obtained, with an HPLC purity of 96.4%, a content of 50.32%, a content yield of 61.1%.

Purification of a Compound of Formula I:

The obtained solid (80 g), silica gel (160 g, 2×) and ethanol (800 mL) were added to the flask; the system was heated to 50-60° C., and stirred at 50-60° C. for 30 minutes, the system was concentrated with a rotary evaporator to dryness for later use; the crude compound of formula I mixed with silica gel was allowed to pass a silica gel column (800 g, 10×), the column was eluted with ethyl acetate until there was basically no former impurities, and the column was eluted with a mixed solution of ethyl acetate and ethanol ($V_{EA}:V_{EtOH}$=100:1-30:1); the components were tested with TLC, components that showed essentially impurity-free by TLC were collected; qualified components were concentrated by a rotary evaporator to (~200 mL); the concentrated residue was exchanged with methanol (~200 mL) twice; the concentrated residue was exchanged with MTBE (~200 mL) twice; MTBE (~300 mL) was added to the concentrated residue; the system was heated to reflux and allowed the system to reflux for 1 hour; the system was cooled to 5-10° C., stirred between 5-10° C. for 2 hours; filtered, the filter cake was washed with MTBE (30 mL); the filter cake was dried with a drying oven under vacuum at 50° C. for 16 hours; 39 g of faint yellow solid was obtained, with an HPLC purity of 99.7% and there were no impurities >0.1%.

The MS-ESI and $^1$H NMR data are consistent with example 21.

Example 29 Preparation of a Compound of Formula I

THF (11 Kg, 12 V), (R)-lactamide (1.64 Kg, 5.0 eq) and $Et_3O$—$BF_4$ (3.50 Kg, 5.0 eq) were added to a 100 L reactor #1, the system was stirred; the materials in #1 were stirred under nitrogen protection for later use; the compound of formula II in THF (5.4 Kg) prepared in example 19 was exchanged by ethanol twice (4.2 Kg×2), ethanol (11.2 Kg, 14V) was added to the system and then the system was transferred to 100 L reactor #2; under nitrogen protection, the system was heated to 45-50° C. (internal temperature); the materials in reactor #1 were added to reactor #2 dropwise within about 1 hour; under nitrogen protection, the temperature of the system was maintained at 45-50° C. for reacting for 3 hours; THF (1.0 Kg, 12V), (R)-lactamide (0.16 Kg, 0.50 eq) and $Et_3O$—$BF_4$ (0.35 Kg, 0.50 eq) were added to a 5 L flask, stirred and dissolved; the solution was added to reactor #2 dropwise and reacted for 2 hours with the temperature maintained; the system was cooled to room temperature, filtered, the filter cake was washed with THF (1.0 Kg); water (2 Kg, 2 V) was added to the filtrate; the filtrate was concentrated with a rotary evaporator to 3 L (2 V-4 V); the concentrated residue was exchanged with ethyl acetate (4 Kg×2) to 3 L (2 V-4 V); water (10 Kg, 10 V) was added to the concentrated residue; the internal temperature was controlled at 20-25° C., 12M HCl was used to adjust the pH of the system to 1-2; activated carbon (0.1 Kg) was added to the system, and the system was stirred at room temperature for 2 hours, and was filtered, the filter cake was washed with water (2 Kg) and 1M HCl (2 Kg); the combined filtrate was extracted with ethyl acetate (3.90 Kg×2), the organic phase was discarded; the internal temperature was controlled at 20-25° C., the pH of the system was adjusted to 9-10 with 50% potassium carbonate solution; the internal temperature was controlled at 15-20° C., the system was stirred for 2 hours, and was filtered, the filter cake was washed with water (2 Kg); the filter cake was triturated with acetone aqueous solution (8.9 Kg, V/V=1:1) at 25-30° C. for 2 hours; the system was cooled to 5-10° C., then the system was triturated for 2 hours, then was filtered, the filter cake was washed with acetone aqueous solution (1.86 Kg, V/V=1:2); the filter cake was dried under vacuum at 50-55° C., 1.3 Kg of solid was obtained, with a content of 39.9%, an HPLC purity of 97.1%.

Purification of a Compound of Formula I:

The above solid (1.3 Kg) and ethanol (6.50 Kg) were added to a rotary flask; the system was heated to 45-55° C., and was stirred for 30 minutes between 45-55° C., the materials were basically dissolved and the solution was clear; silica gel (2.60 kg) was added to the rotary flask, the flask was placed in a 50-60° C. water bath, concentrated under reduced pressure until there was basically no fraction flowing out; the system was exchanged with ethyl acetate (6.50 Kg) until there was basically no fraction flowing out, then stored for later use; a chromatographic column was prepared and washed, silica gel (13.00 Kg, 200-300 meshes) was added to the silica gel column; silica gel column was compacted with ethyl acetate (26.0 Kg); the prepared samples were added to the silica gel column, the samples were placed evenly; the column was eluted with ethyl acetate (52.0 Kg), then the column was eluted with a mixed solution of ethyl acetate and ethanol ($V_{EA}:V_{EtOH}$=100:1, 65.6 Kg), a mixed solution of ethyl acetate and ethanol ($V_{EA}:V_{EtOH}$=80:1, 64.7 Kg), a mixed solution of ethyl acetate and ethanol ($V_{EA}:V_{EtOH}$=50:1, 123.1 Kg), a mixed solution of ethyl acetate and ethanol ($V_{EA}:V_{EtOH}$=30:1, 64.8 Kg); components with a purity >99.0% by HPLC were collected; components with a purity >99.0% by HPLC were pumped into a reactor and concentrated to the minimum stirring volume; 4.0 Kg of methanol was pumped into the reactor, concentrated to the minimum stirring volume; 6.50

Kg×5 of MTBE was pumped into the reactor, concentrated to the minimum stirring volume; 6.50 Kg of MTBE was pumped into the reactor; the system was heated to reflux, and allowed the system to reflux for 1 hour; the system was cooled to 5-10° C., and stirred for 2 hours between 5-10° C.; filtered, the filter cake was washed with MTBE (1.3 Kg); 260 g of wet product was obtained, the filter cake was dried with a drying oven under vacuum between 50-55° C. for 16 hours; 0.250 Kg of product was obtained after drying with an HPLC purity of 100.0%.

The MS-ESI and $^1$H NMR data are consistent with example 21.

In all the following examples of preparing crystal form 1 of a compound of formula I, crystal form A of a hydrochloride of a compound of formula I, crystal form B of a sulfate of a compound of formula I, crystal form C of a hydrobromide of a compound of formula I and crystal form D of a phosphate of a compound of formula I, a compound of formula I was used as a starting material.

Preparation of Crystal Form 1 of a Compound of Formula I

Example 30

A compound of formula I (172.6 g) and acetone (2705 g, ~3500 mL) were added to a 5000 mL three-necked flask; the system was heated to 50-60° C., and was stirred for 2 hours between 50-60° C.; the system was cooled to room temperature (25-30° C.); stirred at room temperature (25-30° C.) for 24 hours; the system was distilled under reduced pressure, the volume of the liquid in the flask was distilled to about 0.8-0.9 L; the liquid was cooled to 15-25° C., about 4.3 Kg purified water was added; the system was stirred at room temperature for 2 hours; then cooled to 5-10° C., then was stirred for 2 hours; the system was subjected to suction filtration, the filter cake was washed with water, the filter cake was dried with an air blower between 50-55° C. for 16 hours; 158.8 g of off-white solid was obtained, with a yield of 92.0%. Upon testing, the off-white solid is crystal form 1 of a compound of formula I. The XRPD pattern, DSC thermogram, TGA thermogram and DVS isotherm plot of the crystal form 1 are shown in FIGS. 1, 2A, 3 and 4 respectively.

Example 31

A compound of formula I (100 mg) was dissolved with acetone (2 mL) between 50-55° C. and the solution was clear, the solution was cooled to room temperature and stirred for about 16 hours, 2 mL of water was added, the system was stirred at room temperature for 2 hours, cooled to 10-15° C., then was stirred for 2 hours, filtered, the solid was collected. Upon testing, the solid is crystal form 1 of a compound of formula I. The XRPD pattern of the crystal form is consistent with FIG. 1.

Example 32

A compound of formula I (200 mg) was dissolved with 9 mL of methanol/water (9:1) at room temperature and the solution was clear, 5 mg of seed crystal of crystal form 1 of a compound of formula I was added, solids were precipitated, the system was stirred overnight at room temperature, water (18 mL) was added to the system, then the system was stirred at room temperature for 4 hours, cooled to 5-10° C. and stirred for 1 hour, subjected to suction filtration, dried under vacuum (about 50° C.) to obtain 180 mg of off-white solid. Upon testing, the off-white solid is crystal form 1 of a compound of formula I. The XRPD pattern of the crystal form is consistent with FIG. 1.

Example 33

The crystallization method that is the same as that in Example 32 was adopted. The crystallization solvent was changed to acetone/water (4:1) to prepare crystal form 1 of a compound of formula I. The XRPD pattern of the crystal form is consistent with FIG. 1.

Crystal form 1 of a compound of formula I can also be prepared with the following method:

Slurrying and Crystallization at Room Temperature

Example 34

About 20 mg of a compound of formula I was weighed then placed into a glass bottle, an appropriate amount of THF was added, the bottle was subjected to ultrasonication for 5 minutes to obtain suspension, the sample bottle was wrapped with tinfoil paper to protect the bottle from light and the bottle was placed on a Labquaker rotator and rotated 360 degrees at room temperature; the suspension sample was centrifuged on Day 10, the solid residue on the bottom was collected, the solvent was evaporated to dryness and an off-white solid was obtained. Upon testing, the off-white solid is crystal form 1 of a compound of formula I. The XRPD pattern of the crystal form is consistent with FIG. 1.

Example 35-Example 40

The crystallization method that is the same as that in Example 34 was adopted. The crystallization solvent was changed to methyl tert-butyl ether, water, acetone, isopropanol, dichloromethane, and ethanol to prepare crystal form 1 of a compound of formula I. Results are shown in Table 6 below.

TABLE 6

| Example number | Crystallization solvent | Crystal form of a compound of formula I |
|---|---|---|
| 35 | Methyl tert-butyl ether | Crystal form 1 |
| 36 | Water | Crystal form 1 |
| 37 | Acetone | Crystal form 1 |
| 38 | Isopropanol | Crystal form 1 |
| 39 | Dichloromethane | Crystal form 1 |
| 40 | Ethanol | Crystal form 1 |

The XRPD pattern of crystal form 1 of a compound of formula I prepared in Examples 35-40 is consistent with FIG. 1.

Slurrying and Crystallization at 50° C.

Example 41

About 20 mg of a compound of formula I was weighed and placed into a glass bottle, an appropriate amount of THF was added, the bottle was subjected to ultrasonication for 5 minutes to obtain suspension, the sample bottle was wrapped with a tinfoil paper to protect the bottle from light and the bottle was placed on a shaking incubator at 50° C. constant temperature for the suspension to be triturated; the suspension sample was centrifuged on Day 10, the solid residue on the bottom was collected, the solvent was evaporated to dryness and an off-white solid was obtained. Upon testing, the off-white solid is crystal form 1 of a compound of formula I. The XRPD pattern of the crystal form is consistent with FIG. 1.

Example 42-Example 45

The crystallization method that is the same as that in Example 41 was adopted. The crystallization solvent was changed to methyl tert-butyl ether, water, acetone and isopropanol to prepare crystal form 1 of a compound of formula I. Results are shown in Table 7 below.

TABLE 7

| Example number | Crystallization solvent | Crystal form of a compound of formula I |
| --- | --- | --- |
| 42 | Methyl tert-butyl ether | Crystal form 1 |
| 43 | Water | Crystal form 1 |
| 44 | Acetone | Crystal form 1 |
| 45 | Isopropanol | Crystal form 1 |

The XRPD pattern of crystal form 1 of a compound of formula I prepared in Examples 42-45 is consistent with FIG. 1.

Example 46

Figure 2A:
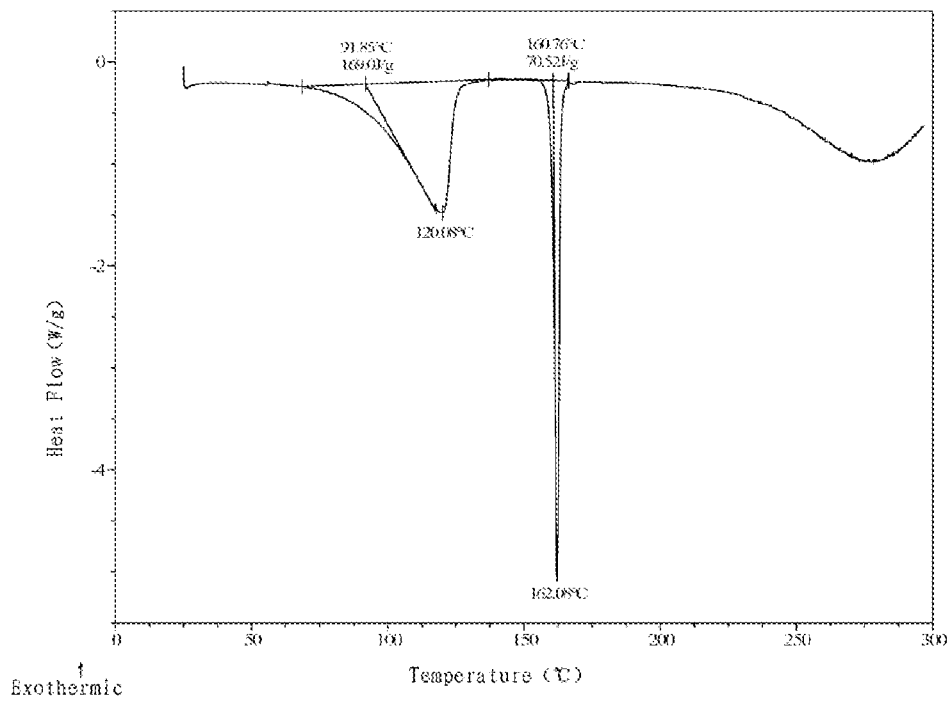
FIG. 2A is the DSC thermogram of crystal form 1 of a compound of formula I of the present invention.
Figure 2B:
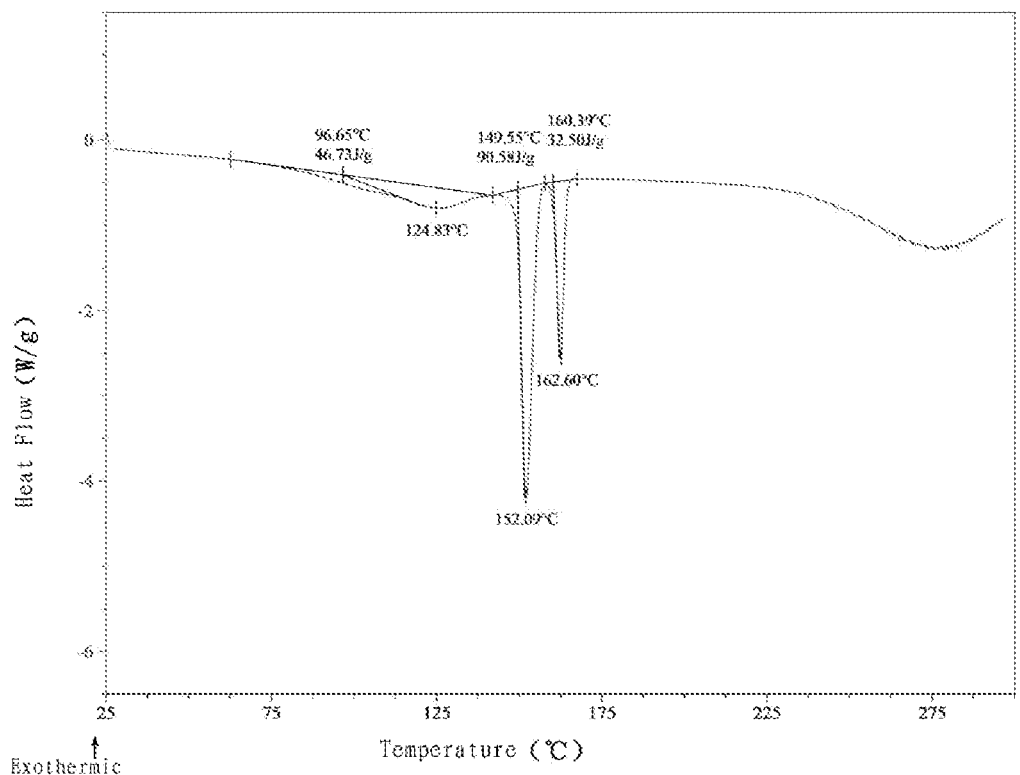
FIG. 2B is another DSC thermogram of crystal form 1 of a compound of formula I of the present invention.
Figure 3:
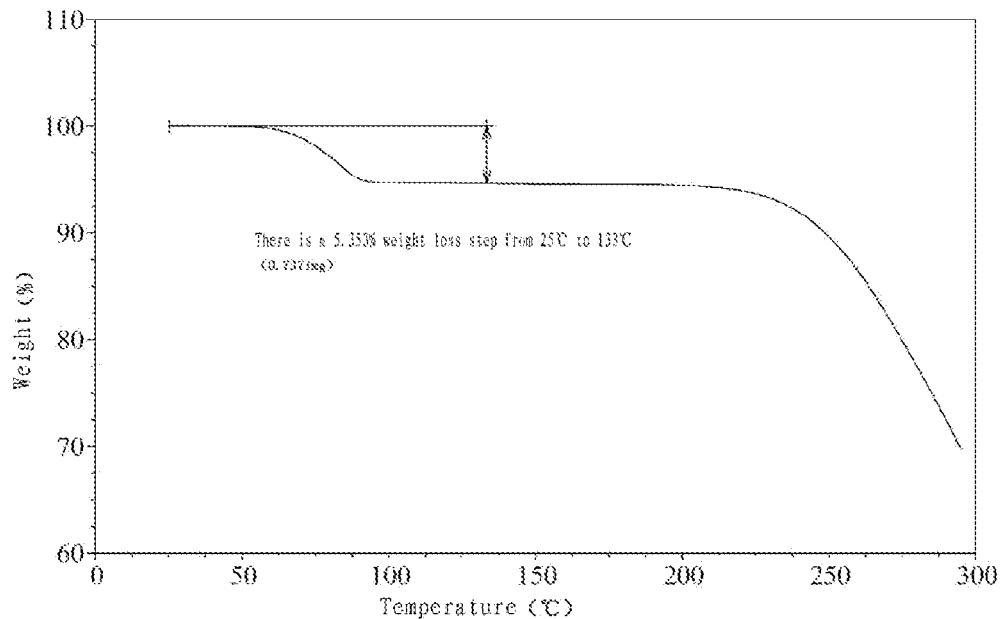
FIG. 3 is the TGA thermogram of crystal form 1 of a compound of formula I of the present invention.
Figure 4:
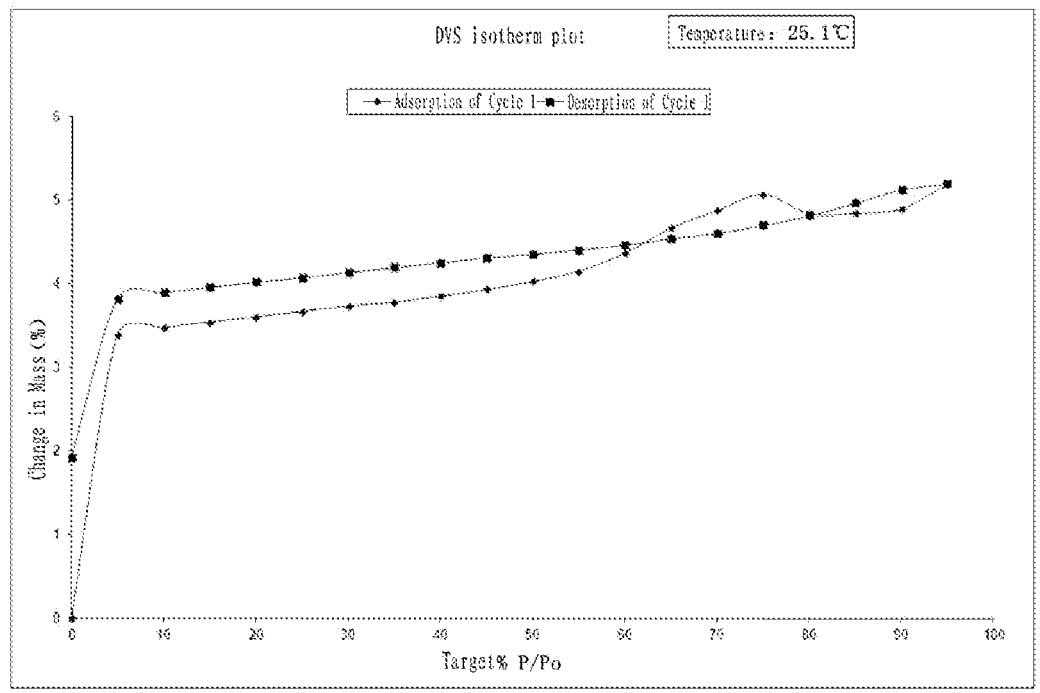
FIG. 4 is the DVS isotherm plot of crystal form 1 of a compound of formula I of the present invention.

The crystallization method that is the same as that in Example 41 was adopted. The crystallization solvent was changed to methanol to prepare crystal form 1 of a compound of formula I. The XRPD of the crystal form is consistent with FIG. 1 and it is crystal form 1 of a compound of formula I. However, the DSC of the crystal form shows an additional peak at about 151° C., as shown in FIG. 2B.

Heating of Saturated Solution—Rapid Cooling and Crystallization

Example 47

About 30 mg of a compound of formula I was weighed and placed into a bottle, an appropriate amount of acetone was added to the bottle, the sample bottle was placed on a magnetic heating stirrer, the temperature of a water bath was controlled at 50±2° C., the rotating speed was 200 rpm, sample was heated to promote dissolution, the temperature was maintained for 15 minutes after the sample was dissolved, the supersaturated solution was filtered with a 0.45 μm membrane when hot, the successive filtrate was transferred to a new bottle, then the bottle was immediately placed into a −20° C. refrigerator overnight, the solvent system with solids precipitated was centrifuged and then the solids were collected, the solvent was evaporated to dryness naturally to obtain an off-white solid. Upon testing, the solid is crystal form 1 of a compound of formula I. The XRPD pattern of the crystal form is consistent with FIG. 1.

Example 48

The crystallization method that is the same as that in Example 47 was adopted. The crystallization solvent as changed to THF to prepare crystal form 1 of a compound of formula I. The XRPD spectrum of crystal form 1 of 1 compound of formula I prepared is consistent with FIG. 1.

Heating of Saturated Solution—Slow Cooling and Crystallization

Example 49

About 30 mg of a compound of formula I was weighed and placed into a bottle, an appropriate amount of acetone was added to the bottle, the sample bottle was placed on a magnetic heating stirrer, the temperature of a water bath was controlled at 50±2° C., the rotating speed was 200 rpm, the sample was heated to promote dissolution, the temperature was maintained for 15 minutes after the sample was dissolved, the supersaturated solution was filtered with a 0.45 μm membrane when hot, the successive filtrate was transferred to a new bottle, then was slowly cooled to room temperature at a rate of 6° C./h, stored in a refrigerator the next day for about 24 hours (2-8° C.), the solvent system with solids precipitated was centrifuged and then the solids were collected, the solvent was evaporated to dryness naturally to obtain an off-white solid. Upon testing, the off-white solid is crystal form 1 of a compound of formula I. The XRPD pattern of the crystal form is consistent with FIG. 1.

Example 50

The crystallization method that is the same as that in Example 49 was adopted. The crystallization solvent was changed to dichloromethane to prepare crystal form 1 of a compound of formula I. The XRPD pattern of the crystal form of a compound of formula I prepared is consistent with FIG. 1.

Anti-Solvent Crystallization

Example 51-Example 62

About 30 mg of a compound of formula I was weighed and placed into a bottle, a certain volume of good solvent was added, the bottle was subjected to ultrasonication at room temperature to disperse the sample to evenly. If the solution was clear, more solid sample was added and ultrasonicating was continued to promote dissolution to obtain a supersaturated solution of the sample in the good solvent. The solution was filtered with a 0.45 μm membrane, the initial filtrate was discarded, the successive filtrate was transferred to a new bottle, an anti-solvent with a volume that is 10 times that of the good solvent was added to the bottle during stirring and the stirring was maintained at 50 rpm, the solvent system with solids precipitated was centrifuged and an off-white solid was obtained. Upon testing, the off-white solid prepared in Examples 51-62 is crystal form 1 of a compound of formula I. The XRPD pattern of the crystal form is consistent with FIG. 1. Results are shown in Table 8 below.

TABLE 8

| Example Number | Crystallization solvent (good solvent - anti-solvent) | Crystal form of a compound of formula I |
| --- | --- | --- |
| 51 | Methanol - water (1:10) | Crystal form 1 |
| 52 | Ethanol - water (1:10) | Crystal form 1 |
| 53 | THF-methyl tert-butyl ether (1:10) | Crystal form 1 |
| 54 | Ethanol-methyl tert-butyl ether (1:10) | Crystal form 1 |
| 55 | Methanol-methyl tert-butyl ether (1:10) | Crystal form 1 |

TABLE 8-continued

| Example Number | Crystallization solvent (good solvent - anti-solvent) | Crystal form of a compound of formula I |
|---|---|---|
| 56 | Acetone-methyl tert-butyl ether (1:10) | Crystal form 1 |
| 57 | Isopropanol-methyl tert-butyl ether (1:10) | Crystal form 1 |
| 58 | THF - dichloromethane (1:10) | Crystal form 1 |
| 59 | Ethanol-dichloromethane (1:10) | Crystal form 1 |
| 60 | Methanol-dichloromethane (1:10) | Crystal form 1 |
| 61 | Acetone-dichloromethane (1:10) | Crystal form 1 |
| 62 | Isopropanol - dichloromethane (1:10) | Crystal form 1 |

Preparation of Crystal Form a of a Hydrochloride of a Compound of Formula I

Example 63

Figure 5:
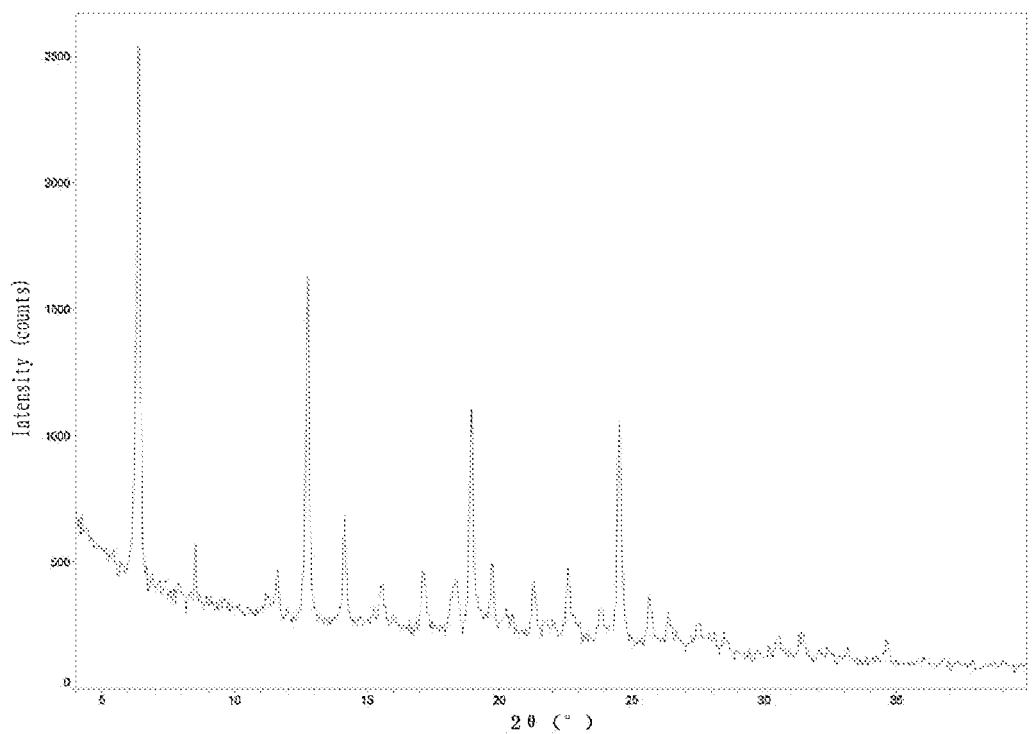
FIG. 5 is the XRPD pattern of crystal form A of a hydrochloride of a compound of formula I of the present invention.
Figure 6:
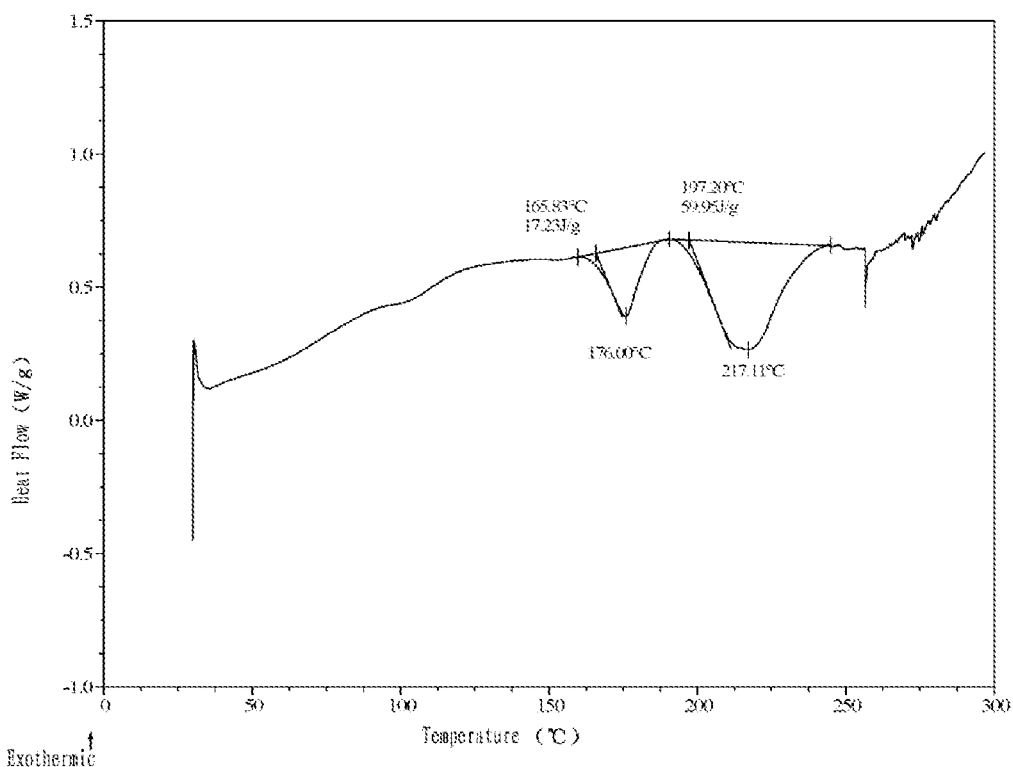
FIG. 6 is the DSC thermogram of crystal form A of a hydrochloride of a compound of formula I of the present invention.
Figure 7:
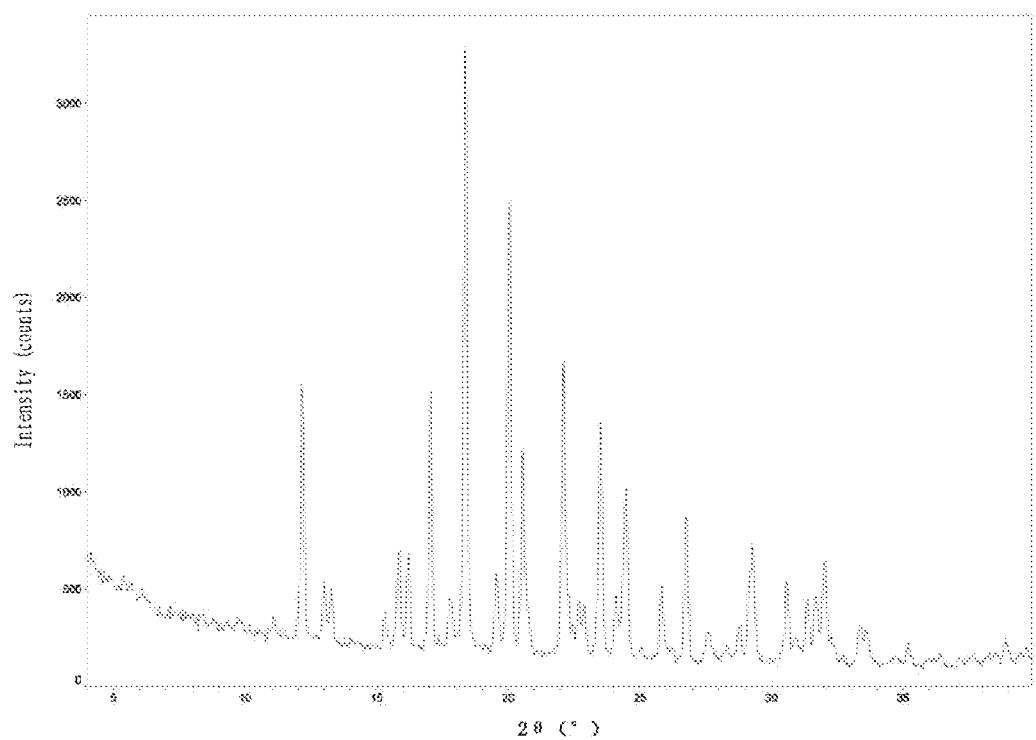
FIG. 7 is the XRPD pattern of crystal form B of a sulfate of a compound of formula I of the present invention.
Figure 8:
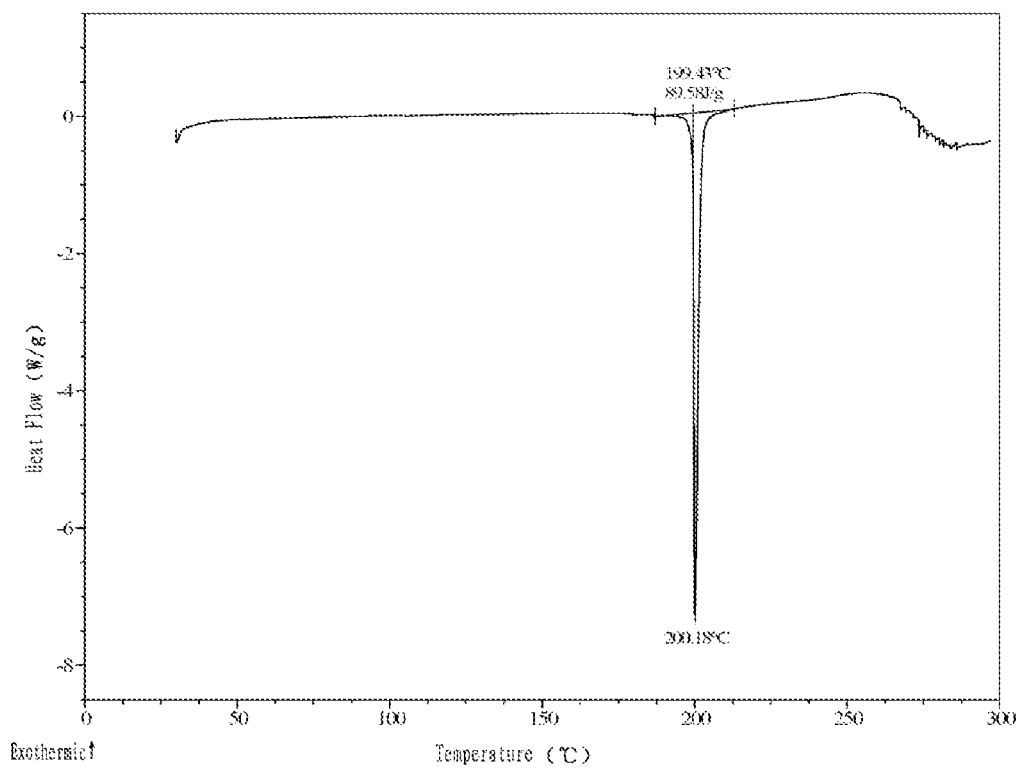
FIG. 8 is the DSC thermogram of crystal form B of a sulfate of a compound of formula I of the present invention.
Figure 9:
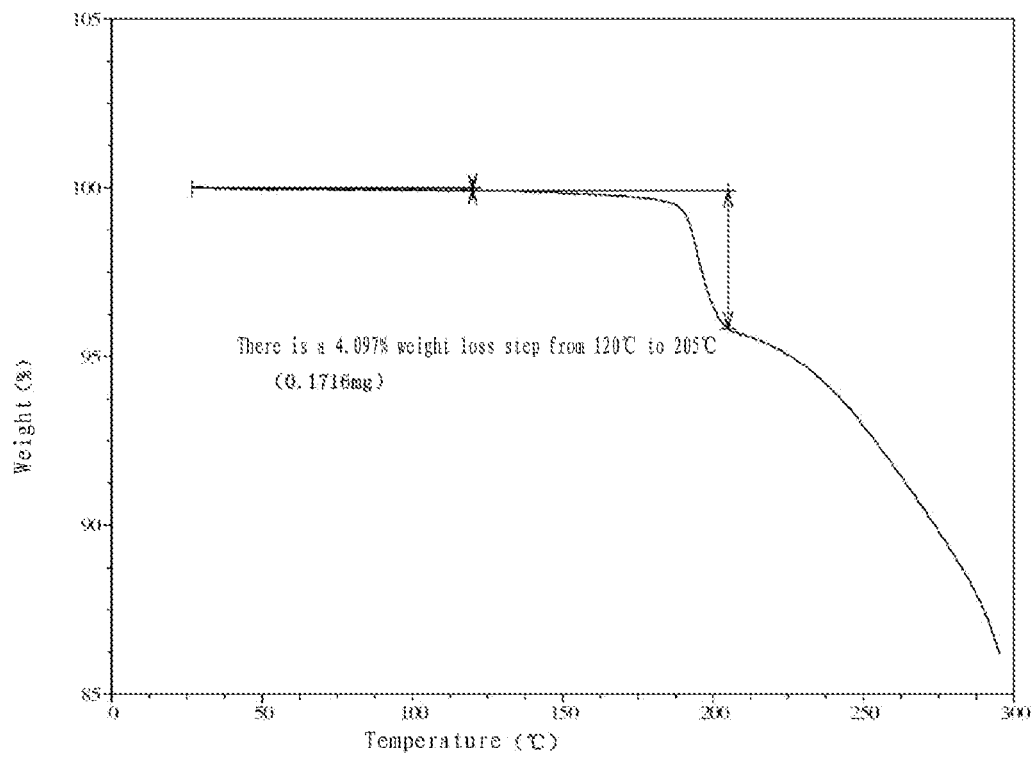
FIG. 9 is the TGA thermogram of crystal form B of a sulfate of a compound of formula I of the present invention.
Figure 10:
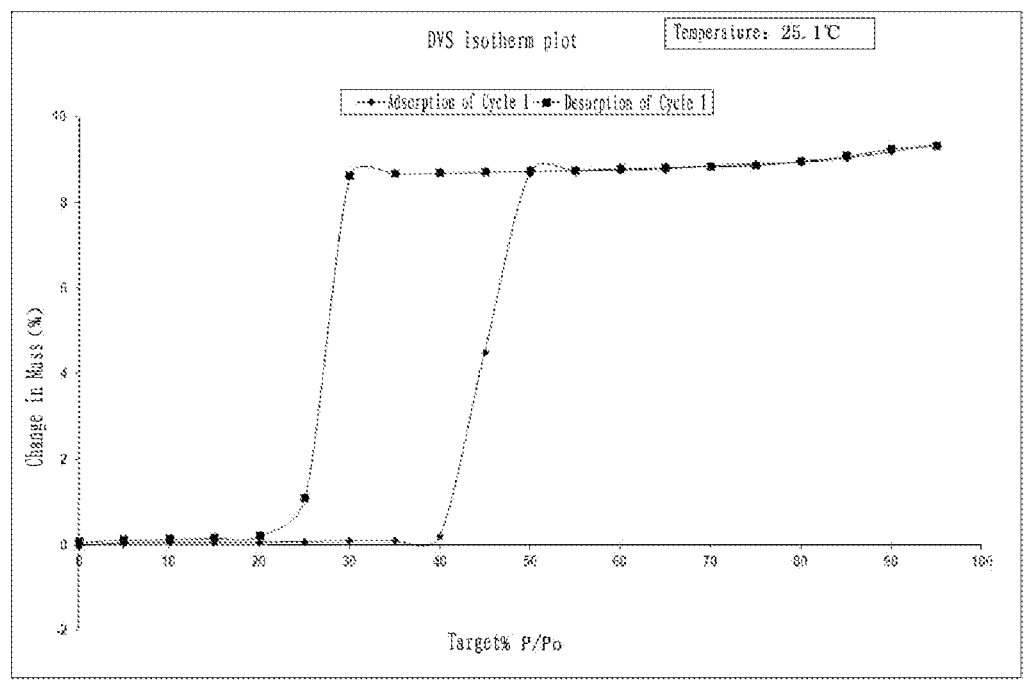
FIG. 10 is the DVS isotherm plot of crystal form B of a sulfate of a compound of formula I of the present invention.

About 200 mg of a compound of formula I was weighed and placed into a bottle, 4 mL of ethanol was added, the bottle was subjected to ultrasonication and heating until the sample was completely dissolved, the sample bottle was placed on a magnetic heating stirrer, magnetic stirring was conducted and during stirring, 1.32 ml of hydrochloric acid in ethanol (the concentration of the hydrochloric acid in ethanol was 50 mg/mL) was slowly added dropwise, a white precipitate was produced, the bottle was covered with a cap tightly at room temperature and was stirred for 1 day, the suspending reaction liquid was then centrifuged, the collected solid was dried under vacuum at 40° C. overnight, a hydrochloride solid of a compound of formula I was obtained. Upon testing, the solid is crystal form A of a hydrochloride of a compound of formula I. The XRPD pattern and the DSC thermogram of the crystal form were shown in FIGS. 5 and 6.

Example 64

About 50 mg of a compound of formula I was weighed and placed into a bottle, 1 mL of ethanol was added, the bottle was subjected to ultrasonication and heating until the sample was completely dissolved, the sample bottle was placed on a magnetic heating stirrer, magnetic stirring was conducted and during stirring, 0.33 ml hydrochloric acid in ethanol (the concentration of the hydrochloric acid in ethanol was 50 mg/mL) was slowly added dropwise, a white precipitate was produced, the bottled was covered with a cap tightly at room temperature and was stirred for 1 day, the suspending reaction liquid was then centrifuged, the collected solid was dried under vacuum at 40° C. overnight, a hydrochloride solid of a compound of formula I was obtained. Upon testing, the solid is crystal form A of a hydrochloride of a compound of formula I. The XRPD pattern of the crystal form is consistent with FIG. 5.

Preparation of Crystal Form B of a Sulfate of a Compound of Formula I

Example 65

About 200 mg of a compound of formula I was weighed and placed into a bottle, 4 mL of ethanol was added, the bottle was subjected to ultrasonication and heating until the sample was completely dissolved, the sample bottle was placed on a magnetic heating stirrer, magnetic stirring was conducted and during stirring, 1.4 ml of sulfuric acid in ethanol (the concentration of the sulfuric acid in ethanol was 50 mg/mL) was slowly added dropwise, a white precipitate was produced, the bottle was covered with a cap tightly at room temperature and was stirred for 1 day, the suspending reaction liquid was centrifuged, the collected solid was dried under vacuum at 40° C. overnight, a sulfate solid of a compound of formula I was obtained. Upon testing, the solid is crystal form B of a sulfate of a compound of formula I. The XRPD pattern, DSC thermogram, TGA thermogram and DVS isotherm plot were shown in FIGS. 7-10.

Example 66

About 50 mg of a compound of formula I was weighed and placed into a bottle, 1 mL of ethanol was added, the bottle was subjected to ultrasonication and heating until the sample was completely dissolved, the sample bottle was placed on a magnetic heating stirrer, magnetic stirring was conducted and during stirring, 0.35 ml of sulfuric acid in ethanol (the concentration of the sulfuric acid in ethanol was 50 mg/mL) was slowly added dropwise, a white precipitate was produced, the bottle was covered with a cap tightly at room temperature and was stirred for 1 day, the suspending reaction liquid was centrifuged, the collected solid was dried under vacuum at 40° C. overnight, a sulfate solid of a compound of formula I was obtained. Upon testing, the solid is crystal form B of a sulfate of a compound of formula I. The XRPD pattern is consistent with FIG. 7.

Preparation of Crystal Form C of a Hydrobromide of a Compound of Formula I

Example 67

Figure 11:
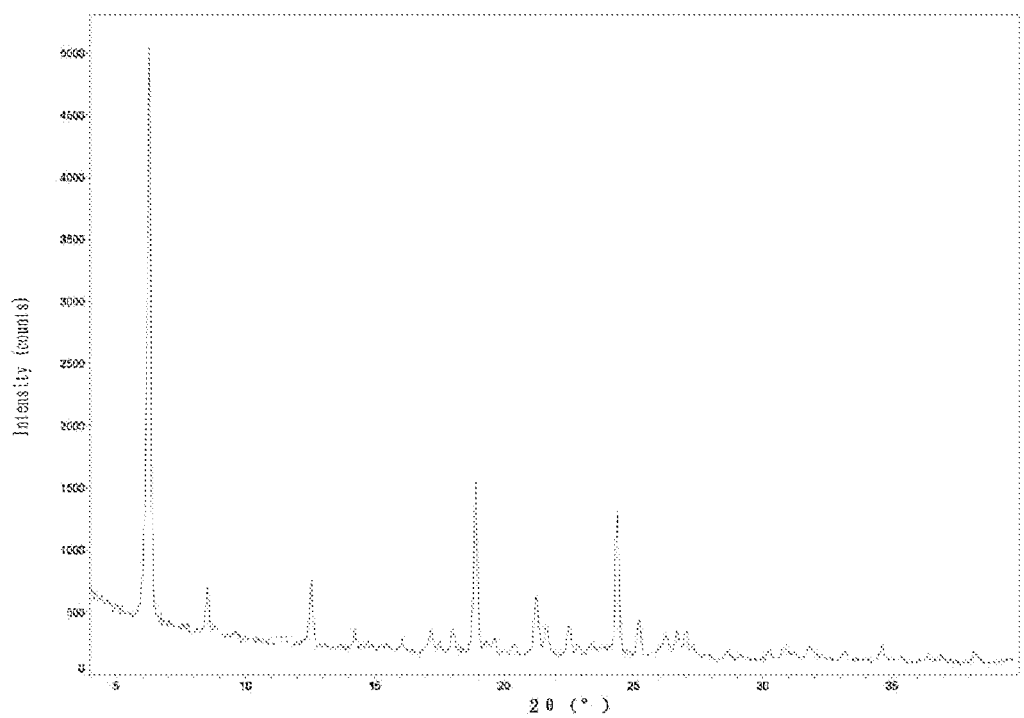
FIG. 11 is the XRPD pattern of crystal form C of a hydrobromide of a compound of formula I of the present invention.
Figure 12:
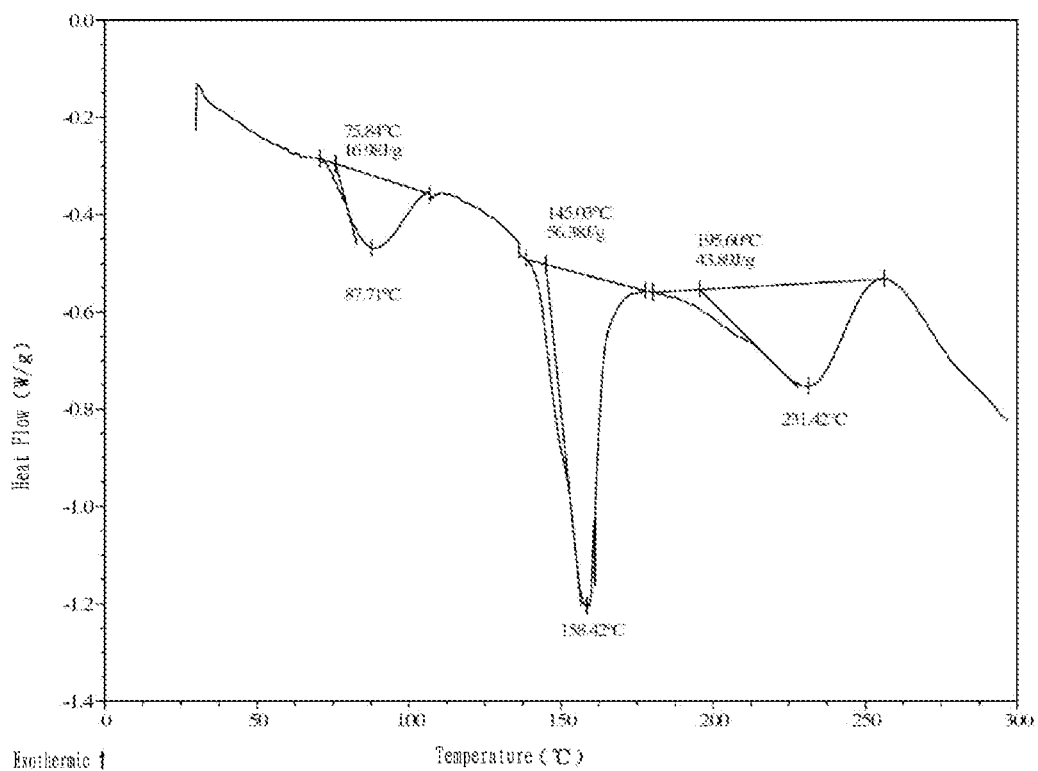
FIG. 12 is the DSC thermogram of crystal form C of a hydrobromide of a compound of formula I of the present invention.
Figure 13:
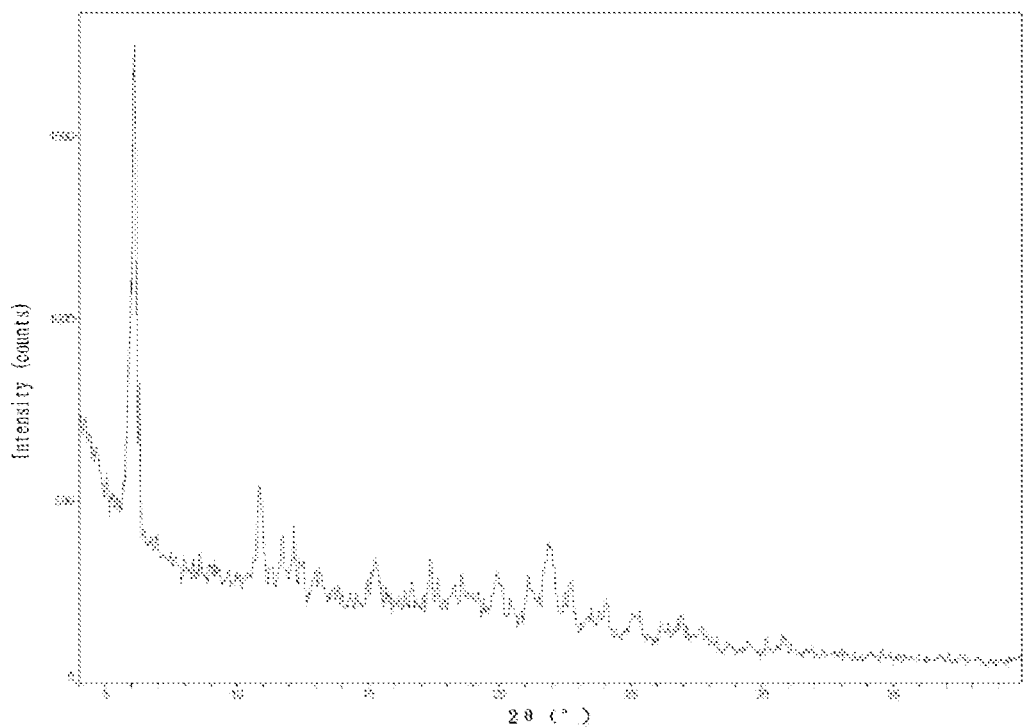
FIG. 13 is the XRPD pattern of crystal form D of a phosphate of a compound of formula I of the present invention.
Figure 14:
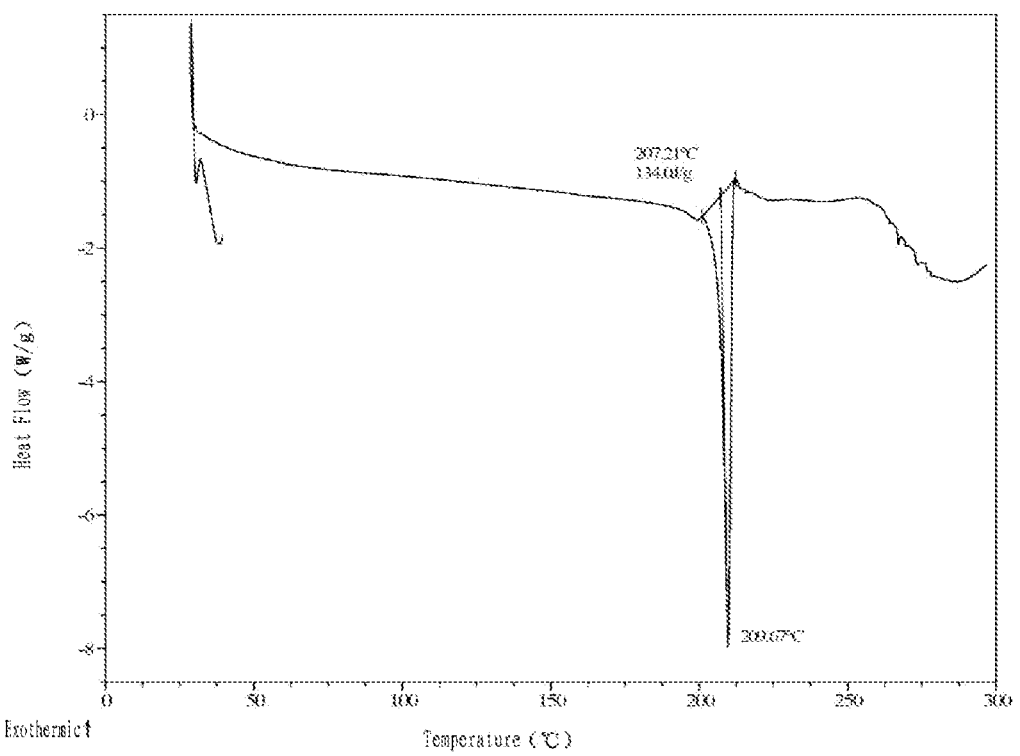
FIG. 14 is the DSC thermogram of crystal form D of a phosphate of a compound of formula I of the present invention.
Figure 15:
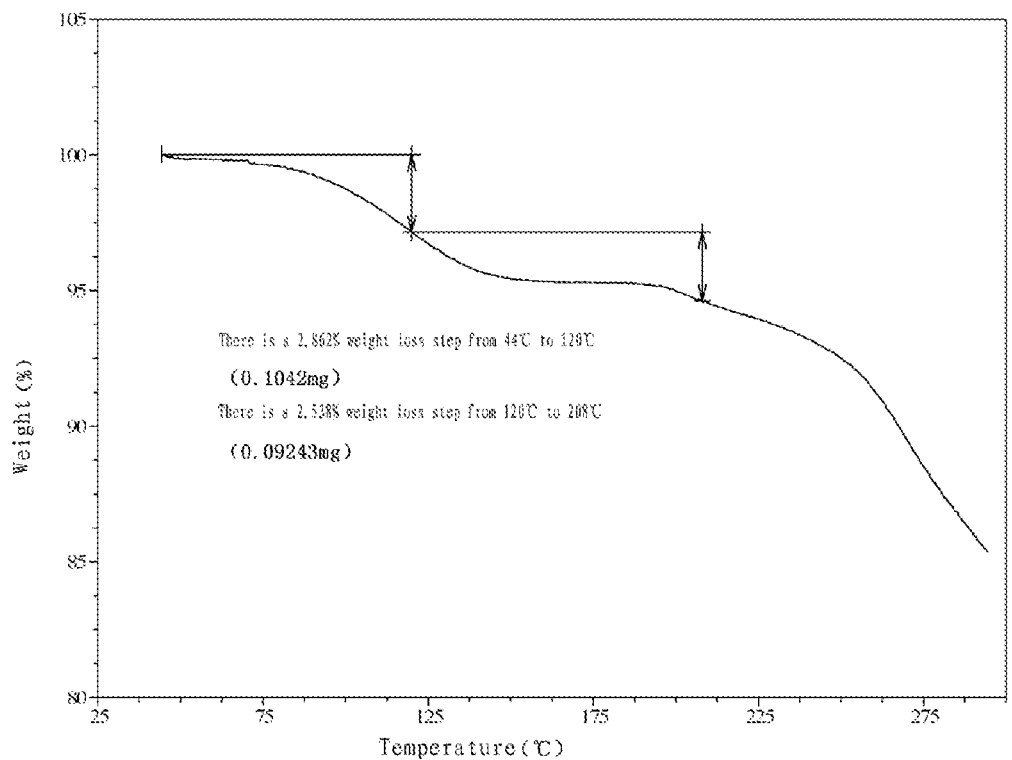
FIG. 15 is the TGA thermogram of crystal form D of a phosphate of a compound of formula I of the present invention.
Figure 16:
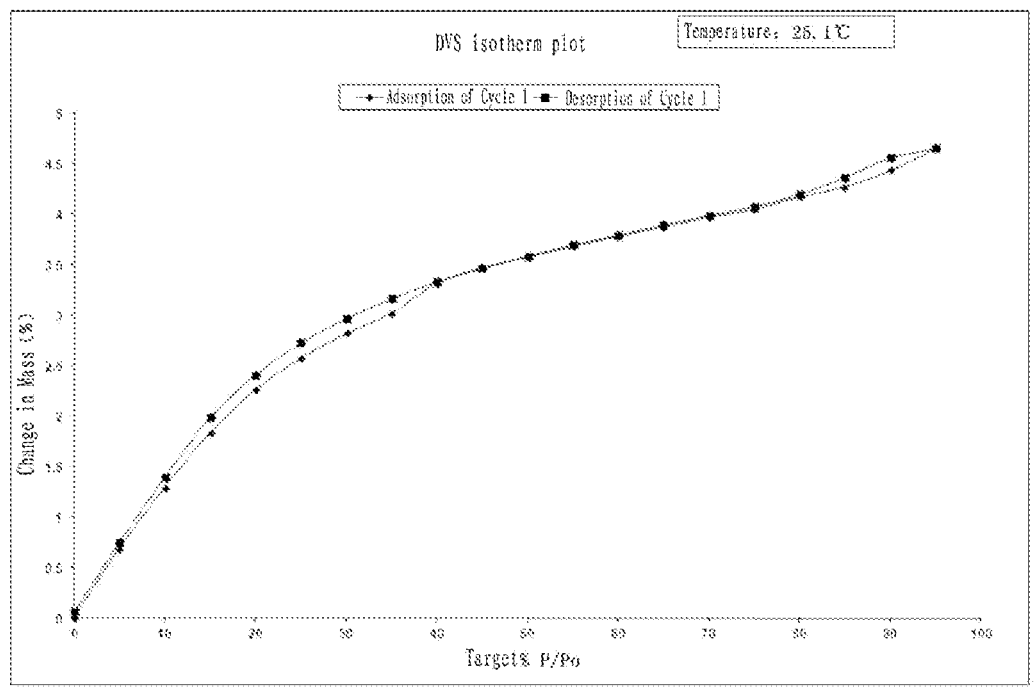
FIG. 16 is the DVS isotherm plot of crystal form D of a phosphate of a compound of formula I of the present invention.
Figure 17:
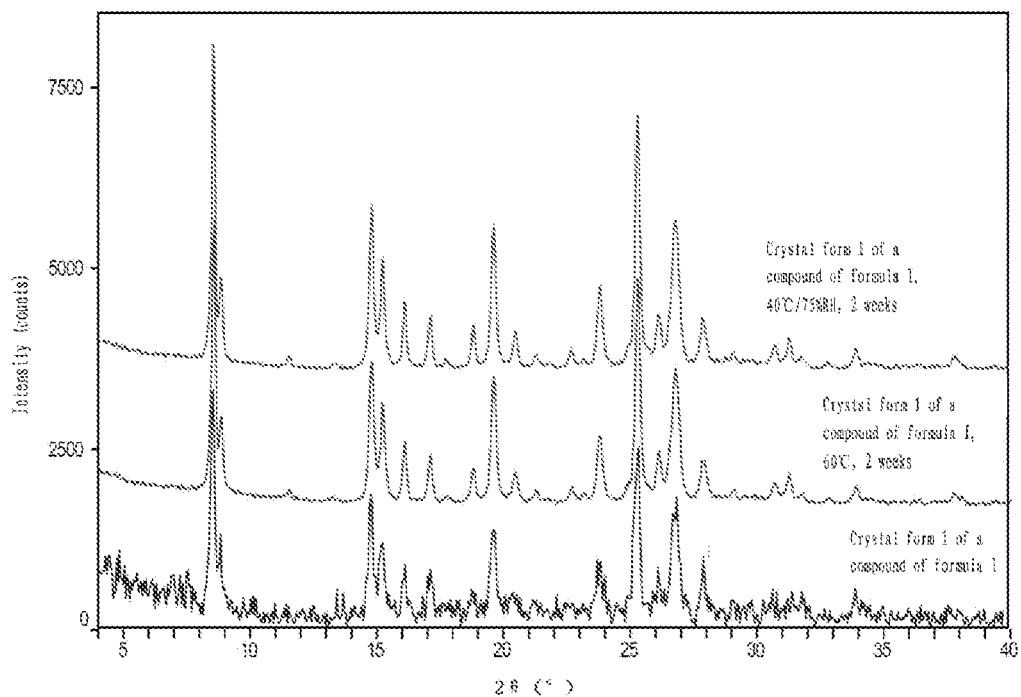
FIG. 17 is the XRPD overlay of crystal form 1 of a compound of formula I of the present invention after being placed at a high temperature and an accelerated condition for 2 weeks.
Figure 18:
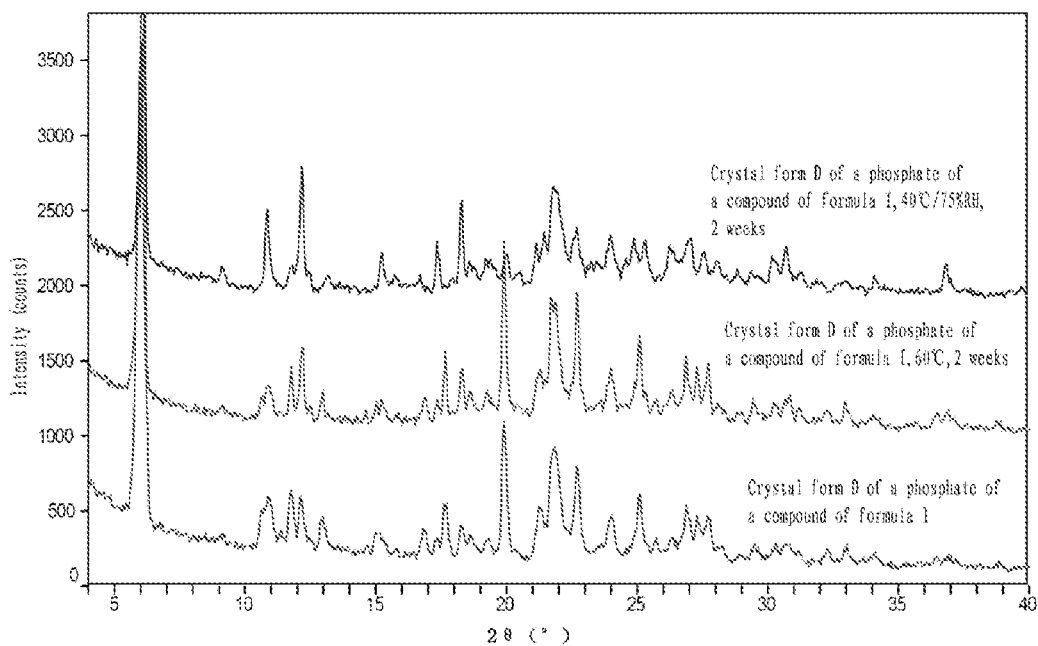
FIG. 18 is the XRPD overlay of crystal form D of a phosphate of a compound of formula I of the present invention after being placed at a high temperature and an accelerated condition for 2 weeks.
Figure 19:
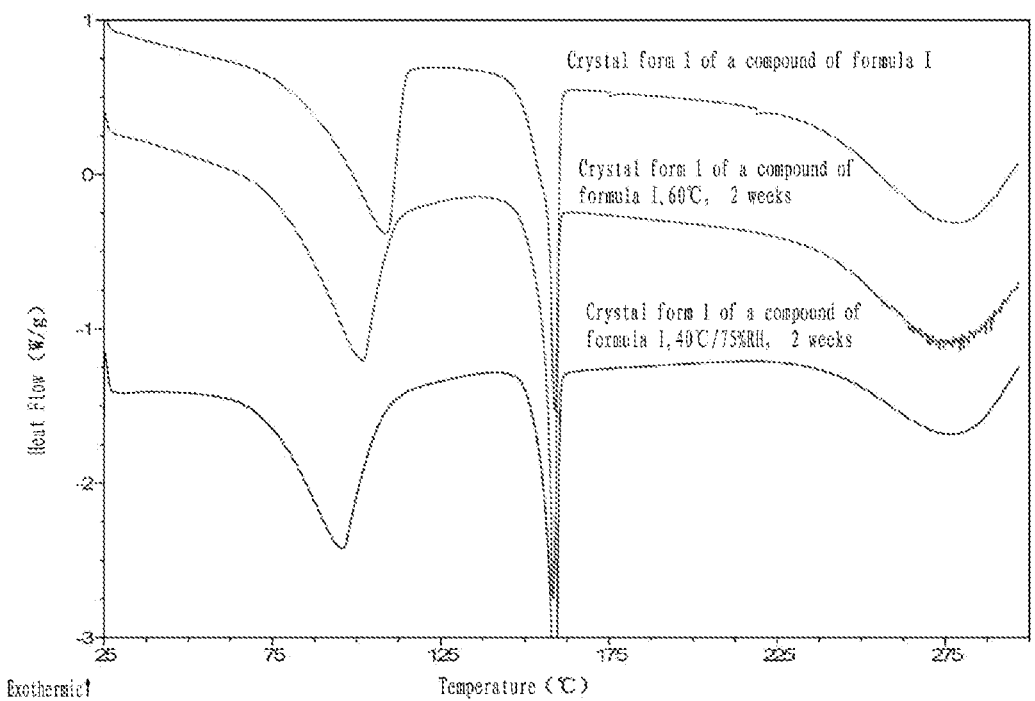
FIG. 19 is the DSC overlay of crystal form 1 of a compound of formula I of the present invention after being placed at a high temperature and an accelerated condition for 2 weeks.
Figure 20:
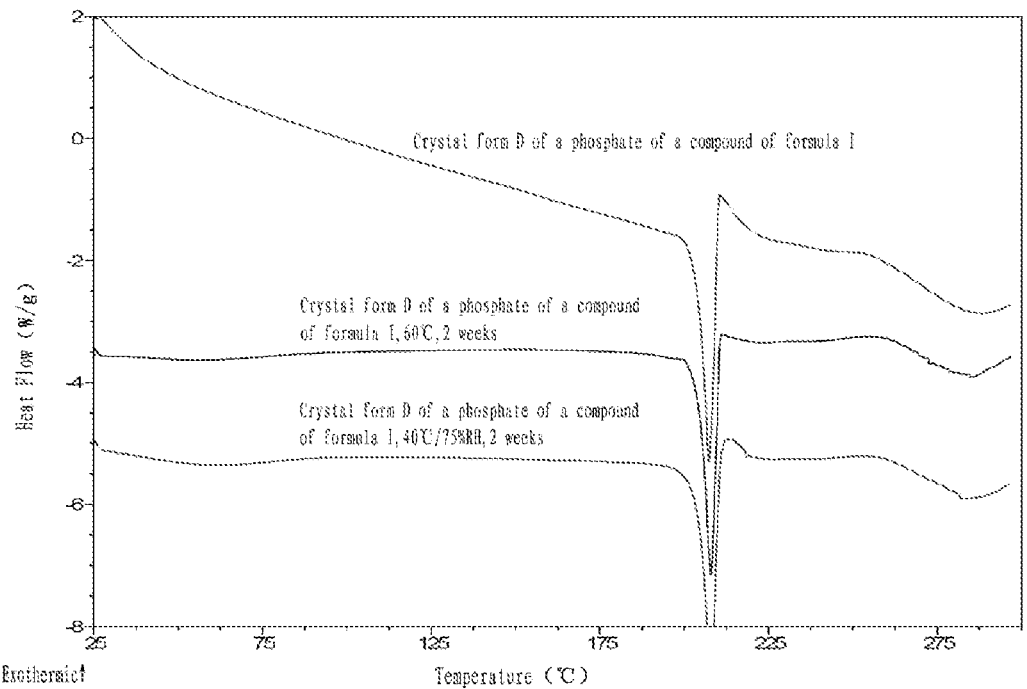
FIG. 20 is the DSC overlay of crystal form D of a phosphate of a compound of formula I of the present invention after being placed at a high temperature and an accelerated condition for 2 weeks.

About 200 mg of a compound of formula I was weighed and placed into a bottle, 4 mL of ethanol was added, the bottled was subjected to ultrasonication and heating until the sample was completely dissolved, the sample bottle was placed on a magnetic heating stirrer, magnetic stirring was conducted and during stirring, 2.4 ml of hydrobromic acid in ethanol (the concentration of the hydrobromic acid in ethanol was 50 mg/mL) was slowly added dropwise, a white precipitate was produced, the bottle was covered with a cap tightly at room temperature and was stirred for 1 day, the suspending reaction liquid was centrifuged, the collected solid was dried under vacuum at 40° C. overnight, a hydrobromide solid of a compound of formula I was obtained. Upon testing, the solid is crystal form C of a hydrobromide of a compound of formula I. The XRPD pattern and DSC thermogram were shown in FIGS. 11 and 12.

Example 68

About 50 mg of a compound of formula I was weighed and placed into a bottle, 1 mL of ethanol was added, the bottle was subjected to ultrasonication and heating until the sample was completely dissolved, the sample bottle was placed on a magnetic heating stirrer, magnetic stirring was conducted and during stirring, 0.60 ml of hydrobromic acid in ethanol solution (the concentration of the hydrobromic acid in ethanol was 50 mg/mL) was slowly added dropwise, a white precipitate was produced, the bottle was covered with a cap tightly at room temperature and was stirred for 1 day, the suspending reaction liquid was centrifuged, the collected solid was dried under vacuum at 40° C. overnight, a hydrobromide solid of a compound of formula I was obtained. Upon testing, the solid is crystal form C of a hydrobromide of a compound of formula I. The XRPD pattern of the crystal form is consistent with FIG. 11.

Preparation of Crystal Form D of a Phosphate of a Compound of Formula I

Example 69

About 200 mg of a compound of formula I was weighed and placed into a bottle, 4 mL of ethanol was added, the bottled was subjected to ultrasonication and heating until the sample was completely dissolved, the sample bottle was placed on a magnetic heating stirrer, magnetic stirring was conducted and during stirring, 1.56 ml of phosphoric acid in ethanol (the concentration of the phosphoric acid in ethanol was 50 mg/mL) was slowly added dropwise, a white precipitate was produced, the bottle was covered with a cap tightly at room temperature and was stirred for 1 day, the suspending reaction liquid was centrifuged, the collected solid was transferred to another bottle, 3-4 ml of a mixed solvent: acetone/water (9/1, V/V) was added, magnetic stirring was conducted at room temperature overnight, the bottle was centrifuged, the solid was collected, and dried under vacuum at 40° C. overnight, a phosphate solid of a compound of formula I was obtained. Upon testing, the solid is crystal form D of a phosphate of a compound of formula I. The XRPD pattern, DSC thermogram, TGA thermogram and DVS isotherm plot are shown in FIGS. 13-16.

Example 70

About 50 mg of a compound of formula I was weighed and placed into a bottle, 1 mL of ethanol was added, the bottled was subjected to ultrasonication and heating until the sample was completely dissolved, the sample bottle was placed on a magnetic heating stirrer, magnetic stirring was conducted and during stirring, 0.39 ml of phosphoric acid in ethanol solution (the concentration of phosphoric acid in ethanol was 50 mg/mL) was slowly added dropwise, a white precipitate was produced, the bottle was covered with a cap tightly at room temperature and was stirred for 1 day, the suspending reaction liquid was centrifuged, the collected solid was transferred to another bottle, 0.75-1 ml of a mixed solvent: acetone/water (9/1, V/V) was added, magnetic stirring was conducted at room temperature overnight, the bottle was centrifuged, the solid was collected, and dried under vacuum at 40° C. overnight, a phosphate solid of a compound of formula I was obtained. Upon testing, the solid is crystal form D of a phosphate of a compound of formula I. The XRPD pattern of the crystal form is consistent with FIG. 13.

Experimental Section

Experimental Example 1 Solid Characterization

DSC, TGA and DVS tests were conducted for crystal form A of a hydrochloride of a compound of formula I, crystal form B of a sulfate of a compound of formula I, crystal form C of a hydrobromide of a compound of formula I and crystal form D of a phosphate of a compound of formula I.

The DSC test results indicated that crystal form B of a sulfate of a compound of formula I (FIG. 8) and crystal form D of a phosphate of a compound of formula I (FIG. 14) had single and higher melting points, indicating that the thermostabilities of the crystal forms were relatively good. Thermodynamic behaviors of crystal form A of a hydrochloride of a compound of formula I (FIG. 6) and crystal form C of a hydrobromide of a compound of formula I (FIG. 12) were complex and their crystallinities were lower. Therefore, further DVS and TGA characterizations were conducted for crystal form B of a sulfate of a compound of formula I and crystal form D of a phosphate of a compound of formula I only.

The DVS test results indicated that crystal form B of a sulfate of a compound of formula I (FIG. 10) and crystal form D of a phosphate of a compound of formula I (FIG. 16) have certain hygroscopicities. Moisture weight gains were 9.4% and 4.7% from 0% RH-95% RH, respectively. There were no significant changes in the crystal forms of the two salts before and after the DVS test.

The TGA test results indicated that crystal form D of a phosphate of a compound of formula I (FIG. 15) had a weight loss of 2.862% from 44° C. to 120° C.

On the basis of the characterization results of the crystal forms of the above four salts, their comparison with crystal form 1 of a compound of formula I is shown in Table 9 below.

TABLE 9

| | Crystal form 1 of a compound of formula I | Crystal form A of a hydrochloride of a compound of formula I | Crystal form B of a sulfate of a compound of formula I | Crystal form C of a hydrobromide of a compound of formula I | Crystal form D of a phosphate of a compound of formula I |
|---|---|---|---|---|---|
| Crystallinity | Excellent | Good | Excellent | Good | Excellent |
| Initial melting point | 161° C. | No obvious melting point | 199° C. | 145° C. | 207° C. |
| TGA | ~5.4% (25-133° C.) | — | — | — | ~2.9% (44-120° C.) |
| Hygroscopicity (95% RH hygroscopic) | 5.2% | — | 9.4% | — | 4.7% |

"—" means not tested

In conclusion, crystal form A of a hydrochloride of a compound of formula I and crystal form C of a hydrobromide of a compound of formula I have wide melting ranges and the melting points are not obvious; the hygroscopicity of crystal form B of a sulfate of a compound of formula I is stronger than that crystal form D of a phosphate of a compound of formula I. Crystal form 1 of a compound of formula I and crystal form D of a phosphate of a compound of formula I have better crystallinities, single melting points, and relatively lower hygroscopicities.

Experimental Example 2 Solubility Test 4 samples, each of crystal form 1 of a compound of formula I and crystal form D of a phosphate of a compound of formula I each with appropriate amount were weighed and placed into a 4 mL transparent glass bottle respectively, 1 mL of water, simulated gastric fluid (SGF), fasted-state simulated intestinal fluid (FaSSIF) and fed-state simulated intestinal fluid (FeSSIF) were added respectively, sample suspension was obtained and quickly placed on a shaker (37° C., 200 rpm) and the shaker was shaked, the samples were observed 5 minutes later, a quantity of samples or medium were supplemented to obtain mild suspension, samples were taken at 30 minutes, 2 hours, 4 hours and 24 hours, respectively, centrifuged for 10 minutes at 12000 rpm, the supernatants were collected, diluted appropriately and then were tested by a higher performance liquid chromatography. The chromatographic conditions were shown in Table 10.

TABLE 10

High performance liquid chromatographic conditions of the solubility test

| Instrument | Agilent 1200 DAD HPLC system |
| --- | --- |
| Chromatographic column | Waters XBridge Shield RP18 4.6 × 150 mm, 3.5 µm |
| Mobile phase | A: 0.05% phosphoric acid aqueous solution B: Acetonitrile |
| Column temperature | 30° C. |
| Detector | DAD |
| Detection wavelength | 232 nm |
| Injection volume | 10 µL |
| Column flow rate | 1.0 mL/min |
| Run time | 10 min |
| Collection time | 10 min |

| Elution procedure | Time (min) | A (%) | B (%) |
| --- | --- | --- | --- |
| | 0.0 | 95 | 5 |
| | 6.0 | 70 | 30 |
| | 7.0 | 5 | 95 |
| | 7.1 | 95 | 5 |
| | 10 | 95 | 5 |

The sample concentrations were calculated with an external standard method. The test results are shown in Table 11.

TABLE 11

| | | Solubility (based on a compound of formula I, mg/mL) | | | |
| --- | --- | --- | --- | --- | --- |
| Sample | Medium | 30 min | 2 h | 4 h | 24 h |
| Crytstal form 1 of a compound of formula I | Water | 0.16 | 0.18 | 0.16 | 0.18 |
| | Simulated gastric fluid (SGF) | 16.52 | 16.71 | 16.88 | 16.42 |
| | Fasted-state simulated intestinal fluid (FaSSIF) | 0.17 | 0.19 | 0.16 | 0.17 |
| | Fed-state simulated intestinal fluid (FeSSIF) | 0.26 | 0.23 | 0.22 | 0.24 |
| Crystal form D of a phosphate of a compound of formula I | Water | 1.85 | 1.78 | 1.73 | 1.80 |
| | Simulated gastric fluid (SGF) | 30.22 | 29.73 | 29.47 | 30.18 |
| | Fasted-state simulated intestinal fluid (FaSSIF) | 0.17 | 0.17 | 0.17 | 0.16 |
| | Fed-state simulated intestinal fluid (FeSSIF) | 0.36 | 0.22 | 0.19 | 0.21 |

The results showed that there was no obvious difference in the equilibrium solubilities (24 h) of crystal form 1 of a compound of formula I and crystal form D of a phosphate of a compound of formula I in FaSSIF and FeSSIF. In water and SGF, equilibrium solubilities (24 h) of crystal form D of a phosphate of a compound of formula I were 1.8 mg/mL and 30.18 mg/mL, respectively, that is, 10 times and 2 times that of the crystal form 1 of a compound of formula I, respectively. Solubilities of crystal form 1 of a compound of formula I and crystal form D of a phosphate of a compound of formula I of the invention meet medicinal requirements.

Experimental Examples 3 Stability Test

About 1 mg of crystal form 1 of a compound of formula I and 1 mg of crystal form D of a phosphate of a compound of formula I samples were weighed and each was placed into a 40 mL transparent glass bottle, the samples were placed in a stability chamber in accelerated conditions (40° C./75% RH, open) and at a high temperature (60° C., sealed) respectively. For the open samples, the bottle cap was removed and the bottle neck was covered with aluminium-foil paper stabbed with pinholes to avoid cross contamination; for the closed samples, each bottle was covered with a cap and sealed tightly. Samples were taken at week 1 and week 2, respectively, after diluted with diluent (acetonitrile/water (1/1) (v/v), the liquid phases were injected according to the chromatographic conditions in Table 12 to determine sample purities.

TABLE 12

| Instrument | Agilent 1200 DAD HPLC system |
| --- | --- |
| Chromatographic column | Agilent ZORBAX SB-Phenyl 150*4.6 mm 3.5 um |
| Mobile phase | A: 20 mM ammonium acetate aqueous solution B: Methanol |
| Column temperature | 40° C. |
| Detector | DAD |
| Detection wavelength | 220 nm |
| Injection volume | 5.0 µL |
| Column flow rate | 1.0 mL/min |
| Run time | 42 min |
| Collection time | 42 min |

| Elution procedure | Time (min) | A (%) | B (%) |
| --- | --- | --- | --- |
| | 0 | 70 | 30 |
| | 14 | 46.5 | 53.5 |
| | 30 | 25 | 75 |
| | 35 | 25 | 75 |
| | 35.01 | 70 | 30 |
| | 42 | 70 | 30 |

The sample purities were calculated with an area normalization method. The test results are shown in Table 13.

TABLE 13

| | Stability study (purity, Area %) | | | | | | |
|---|---|---|---|---|---|---|---|
| | | 60° C. | | | 40° C./75% RH | | |
| Sample | 0 day | 1 week | 2 weeks | Crystal form | 1 week | 2 weeks | Crystal form |
| Crystal form 1 of a compound of formula I | 98.74 | 98.73 | 98.74 | Unchanged | 98.71 | 98.77 | Unchanged |
| Crystal form D of a phosphate of a compound of formula I | 99.13 | 99.11 | 99.11 | Unchanged | 99.11 | 99.10 | Unchanged |

The results indicated that the appearances of crystal form 1 of a compound of formula I and crystal form D of a phosphate of a compound of formula I samples didn't change within 2 weeks and they were off-white powder. There was no significant difference in their purities and the total related substances didn't increase. The XRPD and DSC tests (FIGS. 17-20) indicated that there was no significant difference in the crystal forms and the initial melting points of the two samples compared with those on Day 0, showing that the 2-week physical and chemical stabilities of crystal form 1 of a compound of formula I and crystal form D of a phosphate of a compound of formula I were good at a high temperature (60° C.) and in accelerated conditions (40° C./75% RH).

Experimental Example 4 TYK2 Biochemical Test

An appropriate amount of a compound of formula I was weighed for TYK2 biochemical test.

The test was conducted by Reaction Biology Corp, Malvern, PA (Anastassiadis et al. Nat Biotechnol. 2011; 29(11):1039-45). The step is briefly described as follows.

Reagents:

Basic reaction buffer: 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT and 1% DMSO. The required cofactor was added to each kinase reaction respectively.

Reaction Steps:
1. Preparing the designated substrate in the newly prepared basic reaction buffer;
2. Transferring the required cofactor to the above matrix solution;
3. Transferring the designated kinase to the substrate solution and mixing well slightly;
4. Transferring a compound of formula I in DMSO to the kinase reaction mixture with Acoustic technique (Echo550; nanoliter range), culturing for 20 minutes at room temperature;
5. Introducing $^{33}$P-ATP (specific activity: 10 µCi/µl) to the reaction mixture to trigger a reaction;
6. Culturing at room temperature and conducting a kinase reaction for 2 hours;
7. Plotting the reaction on P81 ion exchange paper;
8. Testing the kinase activity with a filter binding assay.

The test results indicated that a compound of formula I was also a potent TYK2 inhibitor and its $IC_{50}$ was less than 10 nM A person skilled in the art can understand and make some modifications or changes to the invention under the instruction of the present description. These modifications and changes should be in the scope defined in the claims of the invention.

The invention claimed is:

1. A method for preparing a compound of formula I, wherein the synthesis route of the method is as follows:

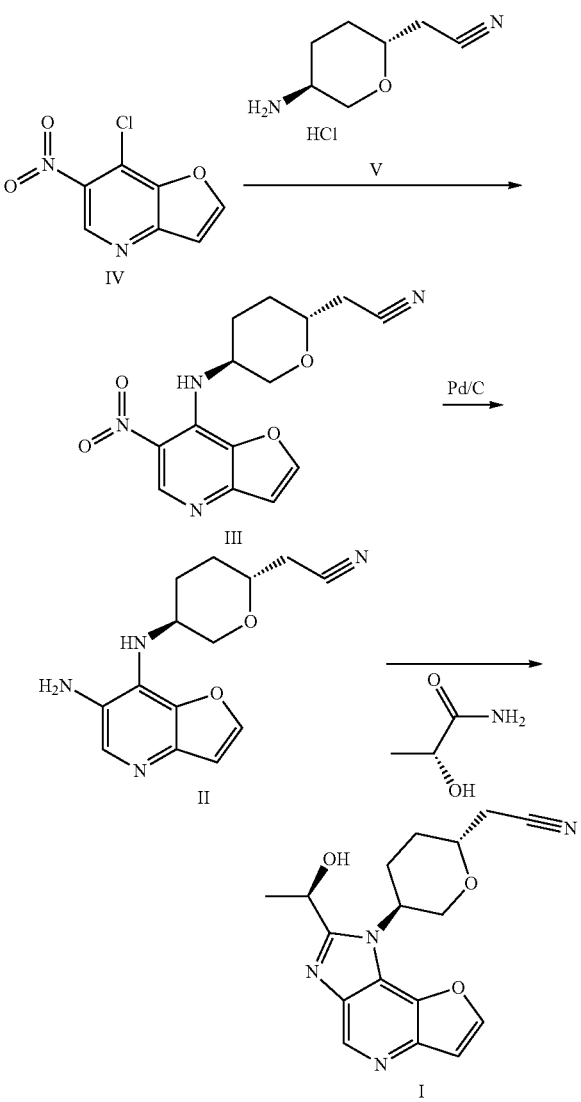

the method comprises the following steps:

step 1:

adding ethanol, a compound of formula IV, a compound of formula V and DIPEA to a reaction container, starting stirring;

heating to raise the temperature to 65-90° C., maintaining the temperature and stirring overnight;
terminating the reaction and lowering the temperature of the system to 15-30° C.;
adding water to the system dropwise and then stirring;
filtering and washing the filter cake;
drying the filter cake to obtain a compound of formula III;
step 2:
adding tetrahydrofuran (THF), the compound of formula III obtained in step 1 and palladium on carbon to a reaction container;
purging the system with nitrogen and then hydrogen;
maintaining the temperature between 20-35° C. and stirring for 16-120 hours under 0.1-1.0 MPa hydrogen pressure;
after the reaction is completed, filtering the reaction liquid and washing the filter cake;
combining the filtrate and concentrating to obtain a compound of formula II concentrate;
step 3:
adding THF, (R)-lactamide and Et$_3$O—BF$_4$ to a first reaction container, starting to stir and dissolving for later use;
adding the above compound of formula II concentrate and ethanol to a second reaction container, and heating the materials in the second container to 40-85° C.;
adding materials in the first reaction container to the second reaction container dropwise, after the addition is completed, maintaining the temperature between 40-85° C. and reacting the mixed materials in the second reaction container for 0.5-6 hours;
after the reaction is completed, adjusting the pH value of the system to 1-3, extracting with an organic solvent or organic solvents, discarding the organic phase, adjusting the pH of the aqueous phase to 9-10 with inorganic alkali aqueous solution, filtering, drying the filter cake to obtain a compound of formula I.

2. The method according to claim 1, wherein in the above step 1: the volume mass ratio of ethanol to the compound of formula IV is between 5:1 and 20:1,
the molar ratio of the compound of formula IV, the compound of formula V and DIPEA is 1:1-1.1:2-3;
after starting stirring, under nitrogen protection, heating to raise the temperature to 65-90° C., maintaining the temperature and stirring for 5-16 hours;
after terminating the reaction, lowering the temperature of the system to 15-25° C.;
the volume mass ratio of water added to the system to the compound of formula IV is between 10:1 and 20:1;
after adding water to the system, stirring for 2-6 hours, at a temperature between 0-30° C.;
the filter cake is washed with ethanol solution, the volume ratio of ethanol to water in the ethanol solution is between 1:1 and 1:2; the volume mass ratio of the ethanol solution to the compound of formula IV is between 2:1 and 10:1; the filter cake is dried under vacuum or dried with an air blower at a temperature between 45-55° C.

3. The method according to claim 1, wherein in the above step 2:
the volume mass ratio of THF to the compound of formula III is between 10:1 and 70:1;
the palladium on carbon is 5% Pd/C, 50% wet palladium on carbon, the mass ratio of the palladium on carbon to the compound of formula III is between 0.15:1 and 0.16:1;

maintaining the temperature at 25-35° C. and stirring for 24-96 hours under 0.5-1.0 MPa hydrogen pressure;
the filter cake is washed with THF, the compound of formula II concentrate obtained by combining the filtrate and concentrating is the compound of formula II in THF, the volume mass ratio of THF for washing to the compound of formula II is between 2:1 and 4:1, exchanging the compound of formula II in THF with ethanol to obtain the compound of formula II in ethanol, wherein the volume mass ratio of ethanol to the compound of formula II is between 2:1 and 5:1.

4. The method according to claim 1, wherein in the above step 3:
the volume mass ratio of THF to the compound of formula II concentrate is between 6:1 and 12:1;
the molar ratio of the compound of formula II concentrate, (R)-lactamide and Et$_3$O—BF$_4$ is 1:4-5:4-5;
the volume mass ratio of ethanol to the compound of formula II concentrate is between 10:1 and 16:1;
after adding the compound of formula II concentrate and ethanol to the second reaction container, under nitrogen protection, heating the materials in the second reaction container to 40-85° C.;
maintaining the temperature at 45-70° C., and reacting the mixed materials in the second reaction container for 2-5 hours;
after the reaction is completed, adjusting the pH of the system to 1-3 with hydrochloric acid, the hydrochloric acid is 1M HCl or 12M HCl; the inorganic alkali aqueous solution is saturated sodium carbonate solution or saturated potassium carbonate solution, preferably saturated potassium carbonate solution;
after the reaction is completed, the organic solvent used for the extraction is dichloromethane or ethyl acetate;
the filter cake is dried under vacuum or dried with an air blower at a temperature between 50-55° C.

5. The method according to claim 1, wherein the compound of formula I obtained in the above step 3 is separated and purified by column chromatography, wherein a mixed solution of ethyl acetate and ethanol is used as an eluent.

6. A crystal form 1 of a compound of formula I,

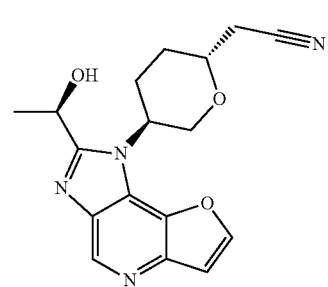

wherein the X-ray powder diffraction pattern of the crystal form shows characteristic peaks at 2theta angles of 8.5°±0.2°, 14.8°±0.2° and 16.1°±0.2°.

7. The crystal form 1 of a compound of formula I according to claim 6, wherein the X-ray powder diffraction pattern of the crystal form shows characteristic peaks at 2theta angles of 8.5°±0.2°, 14.8°±0.2°, 16.1°±0.2°, 17.1°±0.2°, 18.8°±0.2° and 19.6°±0.2°.

8. The crystal form 1 of a compound of formula I according to claim 6, wherein the X-ray powder diffraction pattern of the crystal form shows characteristic peaks at 2theta angles of 8.5°±0.2°, 14.8°±0.2°, 16.1°±0.2°, 17.1°±0.2°, 18.8°±0.2°, 19.6°±0.2°, 23.8°±0.2°, 25.3°±0.2° and 26.1°±0.2°.

9. A method for preparing the crystal form 1 of a compound of formula I according to claim 6, comprising:

method 1:
dissolving a compound of formula I in a solvent, stirring at room temperature, adding water to the above solution of the compound of formula I, stirring, filtering, and drying to obtain crystal form I of the compound of formula I; or method 2:
adding a solvent to a compound of formula I, obtaining suspension of the compound of formula I by ultrasonication, protecting the above suspension from light, stirring, centrifuging, collecting the solid to obtain crystal form I of the compound of formula I; or method 3:
adding solvent to a compound of formula I, stirring at 50-60° C. to dissolve and obtaining solution of the compound of formula I, filtering the above solution when the solution is still hot, then cooling and crystallizing the filtrate between −20-10° C., centrifuging, then collecting the solid to obtain crystal form I of the compound of formula I; or method 4:
adding a first solvent to a compound of formula I, obtaining supersaturated solution of the compound of formula I by ultrasonication, filtering, adding a second solvent to the filtrate and stirring, centrifuging, then collecting the solid to obtain crystal form I of the compound of formula I.

10. The method according to claim 9, wherein, in method 1,
the solvent is selected from the group consisting of acetone, methanol, water and any combinations thereof; the solvent is preferably acetone, or a mixed solvent of methanol and water, or a mixed solvent of acetone and water, wherein the volume ratio of methanol to water in the mixed solvent of methanol and water is 30:1-1:1; the volume ratio of acetone to water in the mixed solvent of acetone and water is 6:1-1:1;
the volume mass ratio of the solvent to the compound of formula I is 20:1-45:1; and the volume mass ratio of water added to the solution of the compound of formula I to the compound of formula I is 20:1-90:1;
dissolving the compound of formula I in the solvent at 50-60° C.;
after dissolving the compound of formula I in the solvent, stirring at room temperature for 0.5-24 hours;
after adding water to the solution of the compound of formula I, stirring at room temperature for 0.5-24 hours, then cooling to 5-15° C. and stirring for 1-4 hours;

in method 2,
the solvent is selected from the group consisting of THF, methyl tertiary-butyl ether, water, acetone, isopropanol, dichloromethane, ethanol and any combinations thereof;
the suspension of the compound of formula I is stirred at room temperature or at 45-55° C.;
the suspension of the compound of formula I is stored away from light and stirred for 6-10 days;

in method 3,
the solvent is selected from the group consisting of acetone, THF, dichloromethane and any combinations thereof;

after filtering the solution of the compound of formula I when the solution is still hot, cooling the solution to room temperature at 6° C./h slowly, then cooling and crystallizing between −20-10° C.;

in method 4,
the first solvent is selected from the group consisting of methanol, ethanol, THF, acetone, isopropanol and any combinations thereof, the second solvent is selected from the group consisting of water, methyl tertiary-butyl ether, dichloromethane and any combinations thereof;
the volume ratio of the first solvent to the second solvent is 1:5-1:20.

11. A crystal form A of a hydrochloride of a compound of formula I,

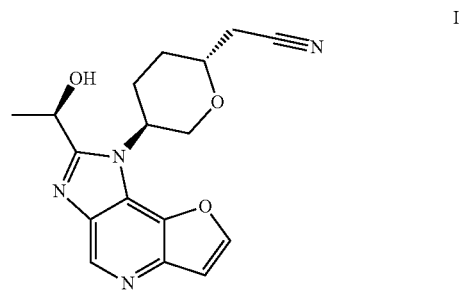 [SMILES: C[C@@H](O)c1nc2cnc3ccoc3c2n1[C@H]1CC[C@H](CC#N)OC1]

wherein the X-ray powder diffraction pattern of the crystal form shows characteristic peaks at 2theta angles of 6.4°±0.2°, 12.8°±0.2°, 14.2°±0.2° and 19.0°±0.2°.

12. The crystal form A of a hydrochloride of a compound of formula I according to claim 11, wherein the X-ray powder diffraction pattern of the crystal form shows characteristic peaks at 2theta angles of 6.4°±0.2°, 8.5°±0.2°, 11.6°±0.2°, 12.8°±0.2°, 14.2°±0.2°, 17.1°±0.2° and 19.0°±0.2°.

13. The crystal form A of a hydrochloride of a compound of formula I according to claim 11, wherein the X-ray powder diffraction pattern of the crystal form shows characteristic peaks at 2theta angles of 6.4°±0.2°, 8.5°±0.2°, 11.6°±0.2°, 12.8°±0.2°, 14.2°±0.2°, 17.1°±0.2°, 19.0°±0.2°, 19.7°±0.2°, 21.3°±0.2° and 24.5°±0.2°.

14. A method for preparing the crystal form A of a hydrochloride of a compound of formula I according to claim 11, comprising:
dissolving a compound of formula I in a solvent to obtain solution of the compound of formula I, adding hydrochloric acid in ethanol to the above solution of the compounds of formula I under stirring, stirring, then centrifuging, collecting the solid and drying to obtain crystal form A of a hydrochloride of a compound of formula I.

15. The method according to claim 14, wherein,
the compound of formula I is dissolved in a solvent under ultrasonication and heating;
the solvent is selected from the group consisting of ethanol, acetone, acetonitrile, isopropanol and any combinations thereof,
the concentration of the hydrochloric acid in ethanol is 30-60 mg/mL, preferably 50 mg/mL;
after adding the hydrochloric acid in ethanol, stirring at room temperature for 4-24 hours.

16. A crystal form of a compound of formula I, wherein the crystal form is selected from the following crystal forms:

crystal form B of a sulfate of a compound of formula I,

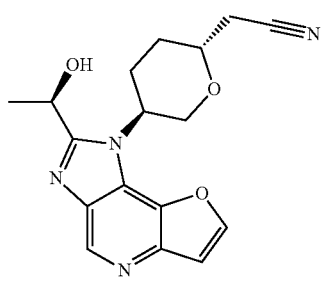

wherein the X-ray powder diffraction pattern of the crystal form B of a sulfate of a compound of formula I shows characteristic peaks at 2theta angles of 12.2°±0.2°, 17.1°±0.2°, 18.4°±0.2° and 20.1°±0.2°; or crystal form C of a hydrobromide of a compound of formula I,

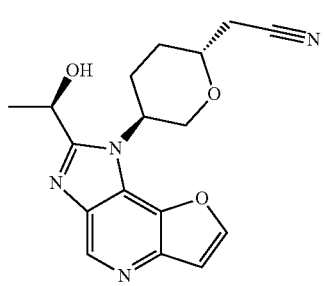

wherein the X-ray powder diffraction pattern of the crystal form C of a hydrobromide of a compound of formula I shows characteristic peaks at 2theta angles of 6.3°±0.2°, 12.6°±0.2° and 18.9°±0.2°.

17. The crystal form of a compound of formula I according to claim 16,
wherein the X-ray powder diffraction pattern of the crystal form B of a sulfate of a compound of formula I shows characteristic peaks at 2theta angles of 12.2°±0.2°, 17.1°±0.2°, 18.4°±0.2°, 19.6°±0.2°, 20.1°±0.2°, 20.6°±0.2° and 22.1°±0.2°;
wherein the X-ray powder diffraction pattern of the crystal form C of a hydrobromide of a compound of formula I shows characteristic peaks at 2theta angles of 6.3°±0.2°, 8.5°±0.2°, 12.6°±0.2°, 18.9°±0.2°, 21.3°±0.2°, 24.4°±0.2° and 25.2°±0.2°.

18. The crystal form of a compound of formula I according to claim 16,
wherein the X-ray powder diffraction pattern of the crystal form B of a sulfate of a compound of formula I shows characteristic peaks at 2theta angles of 12.2°±0.2°, 17.1°±0.2°, 18.4°±0.2°, 19.6°±0.2°, 20.1°±0.2°, 20.6°±0.2°, 22.1°±0.2°, 23.5°±0.2°, 26.8°±0.2° and 29.3°±0.2°.

19. A method for preparing the crystal form of a compound of formula I according to claim 16,
wherein the method for preparing the crystal form B of a sulfate of a compound of formula I comprises:
dissolving a compound of formula I in a solvent to obtain solution of the compound of formula I, adding sulfuric acid in ethanol to the above solution of the compound of formula I under stirring, stirring, then centrifuging, collecting the solid, drying to obtain crystal form B of a sulfate of a compound of formula I;
wherein the method for preparing the crystal form C of a hydrobromide of a compound of formula I comprises:
dissolving a compound of formula I in a solvent to obtain solution of the compound of formula I, adding hydrobromic acid in ethanol to the above solution of the compound of formula I under stirring, stirring, then centrifuging, collecting the solid and drying to obtain crystal form C of a hydrobromide of a compound of formula I.

20. The method according to claim 19, wherein,
in the method for preparing crystal form B of a sulfate of a compound of formula I:
the compound of formula I is dissolved in a solvent under ultrasonication and heating;
the solvent is selected from the group consisting of ethanol, acetone, acetonitrile, isopropanol and any combinations thereof, the concentration of the sulfuric acid in ethanol is 30-60 mg/mL, preferably 50 mg/mL;
after adding the sulfuric acid in ethanol, stirring at room temperature for 4-24 hours;
in the method for preparing the crystal form C of a hydrobromide of a compound of formula I;
the compound of formula I is dissolved in a solvent under ultrasonication and heating;
the solvent is selected from the group consisting of ethanol, acetone, acetonitrile, isopropanol and any combinations thereof;
the concentration of the hydrobromic acid in ethanol is 30-60 mg/mL, preferably 50 mg/mL;
after adding the hydrobromic acid in ethanol, stirring at room temperature for 4-24 hours.

21. A crystal form D of a phosphate of a compound of formula I,

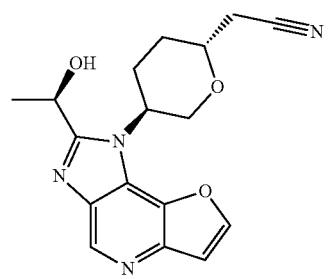

wherein the X-ray powder diffraction pattern of the crystal form shows characteristic peaks at 2theta angles of 6.1°±0.2°, 10.9°±0.2° and 12.2°±0.2°.

22. The crystal form D of a phosphate of a compound of formula I according to claim 21, wherein the X-ray powder diffraction pattern of the crystal form shows characteristic peaks at 2theta angles of 6.1°±0.2°, 10.9°±0.2°, 11.7°±0.2° and 12.2°±0.2°.

23. A method for preparing the crystal form D of a phosphate of a compound of formula I according to claim 21, comprising:
dissolving a compound of formula I in a first solvent to obtain solution of the compound of formula I, adding phosphoric acid in ethanol to the above solution of the compound of formula I under stirring, stirring, then centrifuging, collecting the solid, adding a second solvent to the collected solid, stirring, then centrifuging, collecting the solid and drying to obtain crystal form D of a phosphate of a compound of formula I.

24. The method according to claim 23, wherein,
the compound of formula I is dissolved in the first solvent under ultrasonication and heating;
the first solvent is selected from the group consisting of ethanol, acetone, acetonitrile, isopropanol and any combinations thereof, the second solvent is a mixed solvent of acetone and water, wherein the volume ratio of acetone to water is 7:1-9:1;
the concentration of the phosphoric acid in ethanol is 30-60 mg/mL, preferably 50 mg/mL;
after adding the phosphoric acid in ethanol, stirring at room temperature for 4-24 hours; after adding the second solvent, stirring overnight at room temperature.

25. A pharmaceutical composition comprising crystal form 1 of a compound of formula I according to claim 6, crystal form A of a hydrochloride of a compound of formula I according to claim 11, crystal form B of a sulfate of a compound of formula I according to claim 16, crystal form C of a hydrobromide of a compound of formula I according to claim 16 and/or crystal form D of a phosphate of a compound of formula I according to claim 21.

26. A pharmaceutical formulation comprising crystal form 1 of a compound of formula I according to claim 6, crystal form A of a hydrochloride of a compound of formula I according to claim 11, crystal form B of a sulfate of a compound of formula I according to claim 16, crystal form C of a hydrobromide of a compound of formula I according to claim 16 and/or crystal form D of a phosphate of a compound of formula I according to claim 21.

27. A method for treating JAK1/TYK2-related diseases or conditions in a subject, wherein the diseases or conditions are autoimmune diseases or disorders, rheumatoid arthritis or inflammatory diseases or disorders, and cancers or tumor proliferative diseases or disorders, comprising administering to a subject in need thereof a therapeutically effective amount of crystal form 1 of a compound of formula I according to claim 6, crystal form A of a hydrochloride of a compound of formula I according to claim 11, crystal form B of a sulfate of a compound of formula I according to claim 16, crystal form C of a hydrobromide of a compound of formula I according to claim 16 and/or crystal form D of a phosphate of a compound of formula I according to claim 21.

* * * * *